(12) United States Patent
Yang et al.

(10) Patent No.: US 11,304,939 B2
(45) Date of Patent: Apr. 19, 2022

(54) METHODS FOR TREATING ORAL CANCERS

(71) Applicants: Chang Gung University, Taoyuan (TW); Chang Gung Memorial Hospital, Linkou, Taoyuan (TW)

(72) Inventors: Chia-Yu Yang, Taoyuan (TW); Kai-Ping Chang, Taipei (TW); Chia-Hsun Hsieh, Taoyuan (TW); Chih-Ching Wu, Taoyuan (TW); Chun-Nan Ouyang, Taoyuan (TW); Chiao-Rou Liu, Taoyuan (TW)

(73) Assignees: CHANG GUNG UNIVERSITY, Taoyuan (TW); CHANG GUNG MEMORIAL HOSPITAL, LINKOU, Taoyuan (TW)

( * ) Notice: Subject to any disclaimer, the term of this patent is extended or adjusted under 35 U.S.C. 154(b) by 138 days.

(21) Appl. No.: 15/931,613

(22) Filed: May 14, 2020

(65) Prior Publication Data
US 2021/0353605 A1   Nov. 18, 2021

(51) Int. Cl.
*A61K 31/4439* (2006.01)
*A61K 31/551* (2006.01)
*A61P 35/00* (2006.01)
*A61K 31/5377* (2006.01)
*A61K 33/243* (2019.01)

(52) U.S. Cl.
CPC ...... *A61K 31/4439* (2013.01); *A61K 31/5377* (2013.01); *A61K 31/551* (2013.01); *A61K 33/243* (2019.01); *A61P 35/00* (2018.01)

(58) Field of Classification Search
None
See application file for complete search history.

(56) References Cited

U.S. PATENT DOCUMENTS

2018/0119230 A1*  5/2018  Velculescu ........... C12Q 1/6886

OTHER PUBLICATIONS

Ribeiro et al., Tumor Biology (2014), 35(5), pp. 4687-4695.*
Murugan et al., Cancer Letters (2013), 338(2), pp. 193-203.*
Cohen et al., Oral Oncology (2011), 47(10), pp. 946-950.*
Jee-Hoon Ji et al., Journal of Oral Pathology and Medicine (2009), 38(7), pp. 591-596.*

* cited by examiner

*Primary Examiner* — Brian J Davis

(57) ABSTRACT

Provided herein is a method for treating an oral cancer in a subject. According to embodiments of the present disclosure, the method comprises respectively obtaining a first and a second biological samples from a lesion site and a non-lesion site of the subject; respectively measuring the expression levels of CHEK1, PIK3CA, or PIK3CD in both biological samples by qRT-PCR thereby obtaining a first and a second expression level; determining the ratio of the first to the second expression level; and administering to the subject an effective amount of a checkpoint kinase 1 inhibitor when the ratio for CHEK1 is at least 1.7 or a phosphatidylinositol 3-kinase inhibitor when the ratio for PIK3CA is at least 2.4, or when the ratio for PIK3CD is at least 3.1.

10 Claims, 18 Drawing Sheets
Specification includes a Sequence Listing.

SAS

OC3

OEC-M1

SAS

OEC-M1

OC3

METHODS FOR TREATING ORAL CANCERS

BACKGROUND OF THE INVENTION

1. Field of the Invention

The present disclosure in general relates to the field of cancer treatment. More particularly, the present disclosure relates to a method for treating an oral cancer in a subject in need thereof.

2. Description of Related Art

Cancer is a group of diseases characterized by abnormal cell growth with the potential to invade or spread to other parts of the body, which in turn causes death to the affected individual. According to World Health Organization report, there were 18.1 million new cases of cancer and 9.6 million cancer deaths worldwide in 2018; cancer is the second leading cause of death globally, secondary to cardiovascular diseases. In Taiwan, 2018 marked the 37$^{th}$ year in a row that cancer was the first leading cause of death, with a total number of 48,784. In terms of the mortality rate in Taiwan in 2018, 10 main types of cancer were (1) Tracheal, bronchus, and lung cancer; (2) Liver, gallbladder and biliary tract cancer; (3) Colon and rectum cancer; (4) Female breast cancer; (5) Oral cavity cancer; (6) Prostate cancer; (7) Stomach cancer; (8) Pancreatic cancer; (9) Esophageal cancer; (10) Cervical cancer, in order.

Oral cavity cancer (or oral cancer) refers to cancer occurs on the lining of the lips, mouth, or upper throat, and oral squamous cell carcinomas (OSCC) accounts for up to 90% of all the malignancy of the oral cavity. In 2018, oral cancer occurred globally in about 355,000 people, and resulted in 177,000 deaths, whereas in Taiwan, oral cancer caused 3,027 deaths. Risk factors for oral cancer are mainly cigarette smoking and heavy alcohol consumption, although chewing betel nut, as well as human papilloma virus (HPV) infection have also been reported as one of the major predisposing factors. Current management for OSCC remains surgical excision at an early stage, followed by adjunctive therapy, such as radiation, with or without chemotherapy. Among them, Cisplatin-based chemotherapy or Cetuximab is an instant standard treatment for recurrent/metastatic OSCC. However, treatments of these kinds are not customized, and often bring about severe adverse effects on patients that they suffer from poor quality of life, and usually rehabilitation is required to help return to their normal lives.

In view of the foregoing, there exists in the related art a need for a novel treatment to precisely targeting oral cancers, so as to improve safety and effectiveness in treating oral cancers.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

As embodied and broadly described herein, one aspect of the disclosure is directed to a method for treating an oral cancer in a subject, comprising, (a) respectively obtaining a first and a second biological samples from a lesion site and a non-lesion site of the subject;

(b) respectively measuring the expression levels of a biomarker in the first and the second biological samples by quantitative reverse transcription polymerase chain reaction (qRT-PCR) thereby obtaining a first expression level and a second expression level, wherein the biomarker is CHEK1 gene, PIK3CA gene, or PIK3CD gene;

(c) determining the ratio of the first expression level to the second expression level; and (d) administering to the subject an effective amount of a checkpoint kinase 1 inhibitor or a phosphatidylinositol 3-kinase inhibitor when the biomarker is the CHEK1 gene, and the ratio determined in the step (c) is at least 1.7; or when the biomarker is the PIK3CA gene, and the ratio determined in the step (c) is at least 2.4; or when the biomarker is the PIK3CD gene, and the ratio determined in the step (c) is at least 3.1.

Examples of the CHK1 inhibitor suitable for use in the present disclosure may be (S)-5-(3-Fluorophenyl)-N-(piperidin-3-yl)-3-ureidothiophene-2-carboxamide (AZD7762);

4-(((3S)-1-Azabicyclo(2.2.2)oct-3-yl)amino)-3-(1H-benzimidazol-2-yl)-6-chloroquinolin-2(1H)-one (CHIR-124);

Rabusertib (LY2603618);

Prexasertib (LY2606368);

4-(2,6-dichlorophenyl)-9-hydroxy-6-(3-(methylamino)propyl)pyrrolo[3,4-c]carbazole-1,3(2H,6H)-dione (PD-321852);

(R)-2-amino-2-cyclohexyl-N-(2-(1-methyl-1H-pyrazol-4-yl)-6-oxo-5,6-dihydro-1H-[1,2]diazepino[4,5,6-cd]indol-8-yl)acetamide (PF477736);

(R)-6-Bromo-3-(1-methyl-1H-pyrazol-4-yl)-5-(piperidin-3-yl)pyrazolo[1,5-a]pyrimidin-7-amine (SCH900776);

(R)—N-(4-(3-aminopiperidin-1-yl)-5-bromo-1H-pyrrolo[2,3-b]pyridin-3-yl)nicotinamide;

(R)—N-(4-(3-aminopiperidin-1-yl)-5-bromo-1H-pyrrolo[2,3-b]pyridin-3-yl isobutyramide;

(R)—N-(5-bromo-4-(3-(methylamino)piperidin-1-yl)-1H-pyrrolo[2,3-b]pyridin-3-yl)nicotinamide;

(R)—N-(4-(3-aminopiperidin-1-yl)-5-bromo-1H-pyrrolo[2,3-b]pyridin-3-yl)-5-methylnicotinamide;

(R)—N-(4-(3-aminopiperidin-1-yl)-5-bromo-1H-pyrrolo[2,3-b]pyridin-3-yl)cyclopropane carboxamide;

(R)—N-(4-(3-aminopiperidin-1-yl)-5-bromo-1H-pyrrolo[2,3-b]pyridin-3-yl)-3-methylbutanamide; or (R)—N-(4-(3-aminopiperidin-1-yl)-5-bromo-1H-pyrrolo[2,3-b]pyridin-3-yl)-2-cyclopropylacetamide.

In some specific examples, the CHK1 inhibitor is (S)-5-(3-Fluorophenyl)-N-(piperidin-3-yl)-3-ureidothiophene-2-carboxamide; Prexasertib; or (R)-2-amino-2-cyclohexyl-N-(2-(1-methyl-1H-pyrazol-4-yl)-6-oxo-5,6-dihydro-1H-[1,2]diazepino[4,5,6-cd]indol-8-yl)acetamide.

Examples of the PI3K inhibitor suitable for use in the present disclosure may be (2S)-N1-[5-(2-tert-butyl-4-thiazolyl)-4-methyl-2-thiazolyl]pyrrolidine-1,2-dicarboxamide (A66);

(Z)-5-((5-(4-fluoro-2-hydroxyphenyl)furan-2-yl)methylene)thiazolidine-2,4-dione (AS-252424);

5-(2,2-Difluoro-benzo[1,3]dioxol-5-ylmethylene)-thiazolidine-2,4-dione (AS-604850);

(R)-2-(1-(7-methyl-2-morpholino-4-oxo-4H-pyrido[1,2-a]pyrimidin-9-yl)ethylamino)benzoic acid (AZD6482);

2-amino-N-[7-methoxy-8-(3-morpholinopropoxy)-2,3-dihydroimidazo[1,2-c]quinazolin (BAY 80-6945);

Copanlisib (BAY 80-6946);
8-(6-methoxypyridin-3-yl)-3-methyl-1-(4-(piperazin-1-yl)-3-(trifluoromethyl)phenyl)-1H-imidazo[4,5-c]quinolin-2(3H)-one maleate (BGT226);
Buparlisib (BKM120);
Alpelisib (BYL719);
(5E)-5-{[5-(4-fluorophenyl)furan-2-yl]methylidene}-1,3-thiazolidine-2,4-dione (CAY10505);
5-(2-Amino-8-fluoro-[1,2,4]triazolo[1,5-a]pyridin-6-yl)-N-tert-butylpyridine-3-sulfonamide (CZC24832);
Duvelisib (IPI-145);
2-((6-amino-9H-purin-9-yl)methyl)-5-methyl-3-o-tolylquinazolin-4(3H)-one (IC-87114);
Idelalisib (GS-1101, CAL-101);
Serabelisib (INK 1117);
Taselisib (GDC-0032);
Pictilisib (GDC-0941);
Apitolisib (GDC-0980);
(Z)-5-((4-(pyridin-4-yl)quinolin-6-yl)methylene)thiazolidine-2,4-dione (GSK1059615);
Omipalisib (GSK2126458);
2-methyl-1-(2-methyl-3-(trifluoromethyl)benzyl)-6-morpholino-1H-benzo[d]imidazole-4-carboxylic acid (GSK2636771);
6-[5-[(phenylsulfonyl)amino]-3-pyridinyl]-imidazo[1,2-a]pyridine-3-carboxylic acid, ethyl ester (HS-173);
2-amino-N,N-dimethyl-5-(3-(2-methylpyridin-4-yl)-1H-pyrrolo[2,3-b]pyridine-5-yl)pyridine-3-sulfonamide (HS-527);
2-(4-Morpholinyl)-8-phenyl-4H-1-benzopyran-4-one (LY294002);
Dactolisib (NVP-BEZ235);
Perifosine;
2-Amino-8-[4-(2-hydroxyethoxy)cyclohexyl]-6-(6-methoxypyridin-3-yl)-4-methylpyrido[2,3-d]pyrimidin-7-one (PF-04691502);
Gedatolisib (PF-05212384);
3-(4-morpholinopyrido[3',2':4,5]furo[3,2-d]pyrimidin-2-yl) phenol (PI-103);
2-methyl-5-nitro-2-[(6-bromoimidazo[1,2-a]pyridin-3-yl)methylene]-1-methylhydrazide-benzenesulfonic acid (PIK-75);
N-(2,3-dihydro-7,8-dimethoxyimidazo[1,2-c]quinazolin-5-yl)-3-pyridinecarboxamide (PIK-90);
2-[(4-amino-1H-pyrazolo[3,4-d]pyrimidin-1-yl)methyl]-5-methyl-3-(2-methylphenyl)-4 (3H)-quinazolinone (PIK-293);
2-[[4-amino-3-(3-hydroxyphenyl)-1H-pyrazolo[3,4-d]pyrimidin-1-yl]methyl]-5-methyl-3-(2-methylphenyl)-4 (3H)-quinazolinone (PIK-294);
1-(4-(3-ethyl-7-morpholino-3H-[1,2,3]triazolo[4,5-d]pyrimidin-5-yl)phenyl)-3-(4-(4-methylpiperazine-1-carbonyl)phenyl)urea (PKI-402);
Sonolisib (PX-866);
(S)-2-(2-(2-Methylindolin-1-yl)-2-oxoethyl)-6-morpholinopyrimidin-4(3H)-one (SAR260301);
Pilaralisib (SAR245408);
(2S)-2-[[(2S)-3-Carboxy-2-[[2-[[(2S)-5-(diaminomethylideneamino)-2-[[4-oxo-4-[[4-(4-oxo-8-phenylchromen-2-yl)morpholin-4-ium-4-yl]methoxy]butanoyl]amino]pentanoyl]amino]acetyl]amino]propanoyl]amino]-3-hydroxypropanoate (SF1126);
3-(2,4-Diaminopteridin-6-yl)phenol (TG100713);
Umbralisib (TGR-1202);
5-(9-Isopropyl-8-methyl-2-morpholino-9H-purin-6-yl)pyrimidin-2-amine (VS-5584); Voxtalisib (XL765); or
4,4'-(6-(2-(Difluoromethyl)-1H-benzo[d]imidazol-1-yl)-1,3,5-triazine-2,4-diyl)dimorpholine (ZSTK474).

In some specific examples, the PI3K inhibitor is Alpelisib; Pictilisib; or
(Z)-5-((4-(pyridin-4-yl)quinolin-6-yl)methylene)thiazolidine-2,4-dione.

Alternatively or in addition, the present method further comprises administering to the subject an anti-cancer treatment prior to, in conjunction with, or subsequent to the step (d), in which the anti-cancer treatment is selected from the group consisting of surgery, radiotherapy, chemotherapy, immunotherapy, and a combination thereof.

According to certain embodiments of the present disclosure, the chemotherapy therapy is conducted by administering to the subject a chemotherapeutic agent that is any of Bleomycin, Carboplatin, Capecitabine, Cisplatin, Docetaxel, 5-Fluorouracil (5-FU), Hydroxyurea, Methotrexate, or Paclitaxel. In one particular embodiment, the chemotherapeutic agent is Cisplatin.

According to some embodiments of the present disclosure, the oral cancer is OSCC. Also, according to some embodiments of the present disclosure, the subject is a human.

Many of the attendant features and advantages of the present disclosure will becomes better understood with reference to the following detailed description considered in connection with the accompanying drawings.

BRIEF DESCRIPTION OF THE DRAWINGS

These and other features, aspects and advantages of the present invention will become better understood with reference to the following description, appended claims and the accompanying drawings, where:

FIGS. 1A-1C illustrate the expression of CHEK1 (FIG. 1A), PIK3CA (FIG. 1), and PIK3CD (FIG. 1C) in the 32 paired OSCC patients by qRT-PCR analysis. The expression levels of these genes were determined by the $2^{-\Delta\Delta Ct}$ method and TATA-box binding protein (TBP) was served as an internal control. FIG. 1D is a dot plot depicting the ratio of the gene expressions in tumor tissues to that in adjacent normal tissues of OSCC patients.

FIG. 2A are diagrams depicting the dose-dependent cytotoxic effects of various CHK1 inhibitors (including PF477736, AZD7762 and LY2606368) on OSCC cells SAS and OEC-M1, respectively determined by MTT assay. FIGS. 2B-2C illustrates the dose-dependent cytotoxic effects of PF477736 on OSCC cells determined by colony-forming assay (FIG. 2B), and by Annexin V staining (FIG. 2C). FIG. 2D illustrates the effects of the CHK1 inhibitors on UV-induced phosphorylation of CHK1. FIG. 2E depicts the dose-dependent cytotoxic effects of Cisplatin on OSCC cells SAS, OC3, or OEC-M1 determined by MTT assay. FIG. 2F are bar graphs depicting the effect of PF477736 and Cisplatin on SAS or OC3 cells determined by MTT assay. The data were replicated in three independent experiments. The results were expressed as the mean±S.E.M. The statistical analysis between two groups was performed with Student's t-test. *$p<0.05$; $p<0.01$; *$p<0.001$.

FIG. 3A are line graphs depicting the dose-dependent cytotoxic effects of the PI3K inhibitors (including BYL719, GDC-0941 and GSK1059615) on OSCC cells SAS or OEC-M1 determined by MTT assay.

FIGS. 3B-3C are bar graphs illustrating the dose-dependent cytotoxic effects of BYL719 on OSCC cells determined by colony-forming assay (FIG. 3B), and by Annexin V staining (FIG. 3C). FIG. 3D depicts the effects of the PI3K inhibitors on the phosphorylation of AKT. FIG. 3E depicts the effect of BYL719 and PF477736 on SAS cells determined by MTT assay. FIG. 3F is a bar graph depicting the apoptotic cells in FIG. 3F determined by Annexin V staining. FIG. 3G depicts the effect of GDC-0941 and AZD7762 on SAS cells determined by MTT assay. The data were replicated in three independent experiments. The results were expressed as the mean±S.E.M. The statistical analysis between two groups was performed with Student's t-test. *$p<0.05$; $p<0.01$; *$p<0.001$.

FIG. 5A provides the results of the three OSCC PDX mice (the patient #1 PDX, the patient #2 PDX, and the patient #3 PDX) treated with vehicle controls, Cisplatin alone, PF477736 alone, and PF477736 plus Cisplatin treatments. FIG. 5B are representative photographs of hematoxylin and eosin (H&E) staining and immunohistochemistry (IHC) staining (Ki-67; upper panel); and line graph depicting the corresponding quantitative results (lower panel) from the patient #2 PDX model. FIG. 5C are line graphs depicting the respective changes in the tumor volume of the patient #1 PDX and the patient #2 PDX model treated with vehicle control, BYL719 alone, PF477736 alone, or the combination of PF477736 and BYL719. FIG. 5D provides the results from the patient #2 PDX model determined by of IHC staining (Ki-67; upper panel), and the corresponding quantitative results (lower panel). FIG. 5E are line graphs depicting the changes in the body weight of the patient #2 PDX model after treatments. The tumor volume was measured twice a week, and the mice were monitored for 3 weeks. The data were expressed as the mean±S.E.M. The statistical analysis between two groups was performed with Student's t-test. *: $p<0.05$;**: $p<0.01$.

DESCRIPTION

Figure 1A:
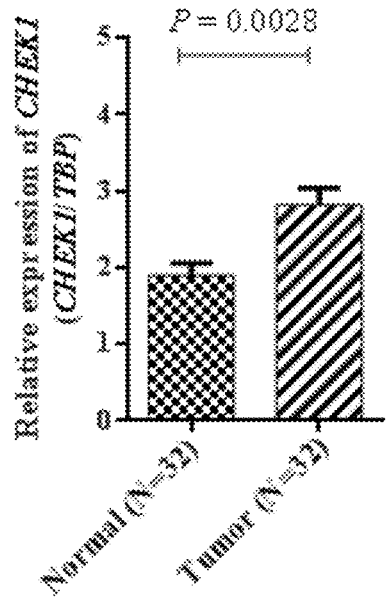
FIGS. 1A-1D depict the expression of CHEK1, PIK3CA, and PIK3CD in OSCC according to one working example of the present disclosure.

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

I. Definition

For convenience, certain terms employed in the specification, examples and appended claims are collected here. Unless otherwise defined herein, scientific and technical terminologies employed in the present disclosure shall have the meanings that are commonly understood and used by one of ordinary skill in the art. Also, unless otherwise required by context, it will be understood that singular terms shall include plural forms of the same and plural terms shall include the singular. Specifically, as used herein and in the claims, the singular forms "a," "an," and "the" include the plural reference unless the context clearly dictates otherwise. Also, as used herein and in the claims, the terms "at least one" and "one or more" have the same meaning and include one, two, three, or more. The practice of the present invention will employ, unless otherwise indicated, conventional techniques of molecular biology, microbiology, recombinant DNA, and immunology, which are within the skill of the art. Such techniques are explained fully in the literature.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about". Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

The terms "treatment" and "treating" as used herein may refer to a curative or palliative measure. In particular, the term "treating" as used herein refers to the application of present method to a subject, who has a cancer, a symptom associated with a cancer, a disease or disorder secondary to a cancer, with the purpose to partially or completely alleviate, ameliorate, relieve, delay onset of, inhibit progression of, reduce severity of, and/or reduce incidence of one or more symptoms or features of a cancer.

The terms "cancer" and "tumor" are used alternatively in the present disclosure, and preferably refer to or describe the physiological condition in mammals that is typically characterized by unregulated cell growth. Cancers in this respect include metastases cancers, and/or drug-resistant cancers. Examples of cancer include, but are not limited to, carcinoma, lymphoma, blastoma, sarcoma, and leukemia or lymphoid malignancies. More particular examples of such cancers include bladder cancer, biliary tract cancer, bone cancer, brain tumor, breast cancer, cervical cancer, colon cancer, colorectal cancer, esophageal cancer, epidermal carcinoma, gastric cancer, gastrointestinal stromal tumor, glioblastoma, glioma, hepatocellular carcinoma, non-Hodgkin's lymphoma, Kaposi's sarcoma, leukemia, lung cancer, lymphoma, intestinal cancer, melanoma, pancreatic cancer, prostate cancer, retinoblastoma, ovary cancer, renal cell carcinoma, spleen cancer, squamous cell carcinoma (e.g.

oral squamous cell carcinoma, epithelial squamous cell carcinoma), thyroid cancer, or thyroid follicular cancer. According to one specific working example, the caner is an oral cancer; more specifically, OSCC.

The term "subject" or "patient" refers to an animal including the human species that is treatable with the methods of the present disclosure. The term "subject" or "patient" intended to refer to both the male and female gender unless one gender is specifically indicated. Accordingly, the term "subject" or "patient" comprises any mammal which may benefit from treatment of cancer. Examples of a "subject" or "patient" include, but are not limited to, a human, rat, mouse, guinea pig, monkey, pig, goat, cow, horse, dog, cat, bird and fowl. In an exemplary embodiment, the subject is a mouse. In another exemplary embodiment, the subject is a human.

The term "lesion" refers to any pathological or traumatic discontinuity of tissue or loss of function of a part. For the purposes as described herein, focal (localized) lesions are of greatest interest, i.e., abnormalities that can be visually attributed to a localized domain, for example, lesions located in the oral cavity. As described herein, a lesion is associated with hyper-proliferative cellular division, which may be malignant, benign, or premalignant in-between after analysis of a biopsy, wherein "premalignant" refers that a benign lesion that is evolving into a malignant lesion. An individual having a lesion may be susceptible or pre-disposed to the disease (e.g., a cancer) and may not yet been diagnosed as having it. The term "susceptible," as described herein, refers to the proneness of an individual towards the development of a certain state (e.g., a certain trait, phenotype or disease), or towards being less able to resist a particular state than the average individual.

The term "biomarker" as used herein refers to a gene, the expression level of which, as measured using a gene product.

The term "at least" as used herein refers to a non-strict inequality which makes a non-equal comparison between two numbers. For example, the phrase "X is at least Y" means X is greater than or equal to Y, or X is not less than Y.

The term "administered," "administering" or "administration" are used interchangeably herein to refer means administering an anti-cancer treatment as described in the present disclosure to a subject in need.

The term "an effective amount" as used herein refers to an amount effective, at dosages, and for periods of time necessary, to achieve the desired therapeutically desired result with respect to the treatment of cancers. For example, in the treatment of a cancer, an agent (i.e., a checkpoint kinase 1 inhibitor or a phosphatidylinositol 3-kinase inhibitor) which decrease, prevents, delays or suppresses or arrests the expression of CHEK1 gene or PIK3CA gene would be effective in preventing the cancer cells from spreading and/or growing. An effective amount of an agent is not required to cure a disease or condition but will provide a treatment for a disease or condition such that the onset of the disease or condition is delayed, hindered or prevented, or the disease or condition symptoms are ameliorated. The specific effective or sufficient amount will vary with such factors as the particular condition being treated, the physical condition of the patient (e.g., the patient's body mass, age, or gender), the type of mammal or animal being treated, the duration of the treatment, the nature of concurrent therapy (if any), and the specific formulations employed and the like. Effective amount may be expressed, for example, as the total mass of the active agent (e.g., in grams, milligrams or micrograms) or a ratio of mass of the active agent to body mass, e.g., as milligrams per kilogram (mg/kg). The effective amount may be divided into one, two or more doses in a suitable form to be administered at one, two or more times throughout a designated time period. Preferably, the effective amount refers to human equivalent dose (HED), which is the maximum safe dosage for use in human subjects. HED may be calculated by following the guidance for industry published by US Food and Drug Administration (FDA) entitled "Estimating the Maximum Safe Starting Dose in Initial Clinical Trials for Therapeutics in Adult Healthy Volunteers" in estimating a maximum safe dosage for use in human subjects.

The term "radiotherapy", also known as radiation therapy, refers to the treatment of cancer and other diseases with an ionizing radiation. Ionizing radiation deposits energy that injures or destroys cells in an area being treated (a "target tissue") by damaging their genetic material, so as to prevent these cells from continuing to grow. Radiation usually causes damages on both cancer cells and normal cells, the latter are better able to recover and function properly. In some embodiments, radiotherapy is used to treat localized solid tumors, such as cancers of the skin, tongue, larynx, brain, breast, prostate, colon, uterus, and/or cervix. In some embodiments, radiotherapy is also used to treat leukemia and lymphoma.

The term "chemotherapy" as used herein refers to the administration of one or more chemotherapeutic agents to a patient in need thereof with the purpose to reduce, prevent, mitigate, limit, and/or delay the growth of neoplasms or metastases in the patient, or kill neoplastic cells directly by necrosis or apoptosis of neoplasms or any other mechanism. The term "chemotherapeutic agent," as used herein refers to any chemical substance known to the clinical practitioner of ordinary skill in the art used for the treatment or amelioration of cancer and/or as an inducer of apoptosis in a patient.

II. Description of The Invention

The present disclosure is based, at least in part, on the discovery that genes, CHEK1, PIK3CA, and/or PIK3CD were differentially expressed between the tumor tissue and the matched adjacent normal tissue of OSCC patients. Therefore, administering a kinase inhibitor (e.g., a checkpoint kinase 1 inhibitor or a phosphatidylinositol 3-kinase inhibitor) to a patient in accordance with the differentially expressed genes (i.e., CHEK1, PIK3CA, and/or PIK3CD) within the patient will improve the efficacy of the kinase inhibitor.

1. Methods for Treating Cancers

Accordingly, the first aspect of the present disclosure is directed to a method for treating a cancer in a subject. The method comprises, (a) respectively obtaining a first and a second biological samples from a lesion site and a non-lesion site of the subject;

(b) respectively measuring the expression levels of a biomarker in the first and the second biological samples by qRT-PCR thereby obtaining a first expression level and a second expression level, wherein the biomarker is CHEK1 gene, PIK3CA gene, or PIK3CD gene;

(c) determining the ratio of the first expression level to the second expression level; and (d) administering to the subject an effective amount of a checkpoint kinase 1 inhibitor or a phosphatidylinositol 3-kinase inhibitor when the biomarker is the CHEK1 gene, and the ratio determined in the step (c) is at least 1.7; or when the biomarker is the PIK3CA gene, and the ratio determined in the step (c) is at least 2.4; or when the biomarker is the PIK3CD gene, and the ratio determined in the step (c) is at least 3.1.

According to preferred embodiments of the present disclosure, the present method may be used to treat cancers as described above. Preferably, the present method may be used to treat an oral cancer, such as tumor from the floor of mouth, gingivae cancer, lip cancer, major salivary gland cancer, oropharynx cancer, OSCC, other mouth cancer, palate cancer, and tongue cancer. In some specific embodiments, the cancer treatable by the present method is OSCC.

According to some embodiments of the present disclosure, the subjects treatable by the present method are those described above. In some embodiments, the subject that would benefit from the present method is a mouse. In other embodiments, the subject suitable for treating with the present method is a human.

To start with, paired samples, which are biological samples respectively taken from a lesion site and a non-lesion site from the subject, are termed a first and a second biological samples (the step (a)). Since the first biological sample is the one taken from the legion site, thus the second biological sample is taken from a normal tissue, and may be any one of a skin epithelium, nasal mucosa, oral mucosa, buccal epithelium, palatal epithelium, sublingual epithelium, sub-mucosa, rectal epithelium, vaginal epithelium, intrathecal tissue, intramuscular tissue, intravenous tissue, ligament, or tendon. Preferably, the second biologic sample is an oral mucosa adjacent to the lesion site. According to alternative embodiments of the present disclosure, the first biological sample and the second biological sample may be from different subjects. For example, the first biological sample is from a lesion site of the subject affiliated with cancers, whereas the second biological sample is from a non-lesion site of a healthy donor.

Then, both the first and second biological samples are subjected to gene expression analysis directed to particular biomarker(s) (the step (b)). The biomarker to be detected in the present method (i.e., in the step (b)) may be CHEK1 gene or PIK3CA gene, or optionally, PIK3CD. In some embodiments, the respective levels of CHEK1 gene in the first and second biological samples are determined. In other embodiments, the respective levels of PIK3CA gene in the first and second biological samples are determined. Alternatively, in still other embodiments, the respective levels of PIK3CD gene in the first and second biological samples are determined. Technologies suitable for assessing gene expression are well known in the art, which include but are not limited to, genome-wide expression profiling using expressed sequence tag (EST) analysis, serial analysis of gene expression (SAGE), DNA microarrays, massively parallel signature sequencing (MPSS), RNA sequencing (RNA-seq), qRT-PCR, digital polymerase chain reaction (dPCR), two-dimensional gel electrophoresis (2-D electrophoresis), tissue array, immunohistochemistry (IHC) staining and etc. In some embodiments, the gene expression is analyzed by RNA-seq. In other embodiments, the gene expression is analyzed by qRT-PCR. In still other embodiments, IHC staining is used. Preferably, in the present method, gene expression is analyzed by qRT-PCR.

Alternatively or optionally, to minimize individual differences from one individual to another, the determined levels of the biomarkers are normalized. As used herein, the term "normalized or normalization" when applies to a gene refers to the normalized level of a gene product, e.g. the normalized value determined for the RNA expression level of a gene or for the polypeptide expression level of a gene. Usually, the normalization means dividing the value of the biomarker in the sample by the value of a housekeeping gene. A "biomarker" is defined as a laboratory measurement that reflects the activity of a disease process, in other words, biomarkers quantitatively correlate (either directly or inversely) with disease progression. A "housekeeping gene" refers to a gene that is constitutively expressed at a relatively constant level across many or all known conditions, because it encodes for a protein that is constantly required by the cell, hence, it is essential to a cell and always present under any conditions. It is assumed that its expression is unaffected by experimental conditions. The protein it encodes is generally involved in the basic functions necessary for the sustenance or maintenance of the cell. According to embodiments of the present disclosure, the housekeeping gene may be any one of β-actin (ACTB), glyceraldeyde-3-phosphate dehydrogenase (GAPDH), β-glucuronidase (GUSB), hydroxymethylbilane synthase (HMBS), hypoxanthine guanine phosphoribosyl transferase 1 (HPRT1), TATA-box binding protein (TBP), or 18S ribosomal RNA (rRNA). In one specific embodiment, the housekeeping gene is TBP.

After the gene expression level (e.g., CHEK1, PIK3CA or PIK3CD) in the first and second biological samples were determined and optionally normalized, then the ratio of the first expression level (i.e., the level of a biomarker in the first biological sample) to the second expression level (i.e., the level of the same biomarker in the second biological sample) is calculated via dividing the first expression level by the second expression level, so that the relative expression of the biomarker (e.g., CHEK1, PIK3CA, PIK3CD or a combination thereof) between the first and second biological samples (i.e., the lesion and normal sites) is determined (i.e., the step (c)).

Then, based on the respective ratio of the biomarkers determined in the step (c), the subject suffered from OSCC is treated. In the present method, when the ratio of a specific biomarker (e.g., CHEK1, PIK3CA or PIK3CD) is above a pre-determined threshold, then a checkpoint kinase 1 inhibitor or a phosphatidylinositol 3-kinase inhibitor is administered to the subject. For the biomarker CHEK1 gene, the pre-determined threshold is 1.7; for the biomarker PIK3CA gene, the pre-determined threshold is 2.4; as to the biomarker PIK3CD gene, the pre-determined threshold is 3.1. Accordingly, the OSCC subject may be treated with the checkpoint kinase 1 inhibitor or the phosphatidylinositol 3-kinase inhibitor if the ratios of CHEK1, PIK3CA and PIK3CD genes between the lesion and normal sites are independently at least 1.7, 2.4 or 3.1.

Examples of CHK1 inhibitors suitable for use in the present method include, but are not limited to, (S)-5-(3-Fluorophenyl)-N-(piperidin-3-yl)-3-ureidothiophene-2-carboxamide (AZD7762);

4-(((3S)-1-Azabicyclo(2.2.2)oct-3-yl)amino)-3-(1H-benzimidazol-2-yl)-6-chloroquinolin-2(1H)-one (CHIR-124);

Rabusertib (LY2603618);

Prexasertib (LY2606368);

4-(2,6-dichlorophenyl)-9-hydroxy-6-(3-(methylamino)propyl)pyrrolo[3,4-c]carbazole-1,3(2H,6H)-dione (PD-321852);

(R)-2-amino-2-cyclohexyl-N-(2-(1-methyl-1H-pyrazol-4-yl)-6-oxo-5,6-dihydro-1H-[1,2]diazepino[4,5,6-cd]indol-8-yl)acetamide (PF477736);

(R)-6-Bromo-3-(1-methyl-1H-pyrazol-4-yl)-5-(piperidin-3-yl)pyrazolo[1,5-a]pyrimidin-7-amine (SCH900776);

(R)—N-(4-(3-aminopiperidin-1-yl)-5-bromo-1H-pyrrolo[2,3-b]pyridin-3-yl)nicotinamide (R)—N-(4-(3-aminopiperidin-1-yl)-5-bromo-1H-pyrrolo[2,3-b]pyridin-3-yl isobutyramide;
(R)—N-(5-bromo-4-(3-(methylamino)piperidin-1-yl)-1H-pyrrolo[2,3-b]pyridin-3-yl)nicotinamide;
(R)—N-(4-(3-aminopiperidin-1-yl)-5-bromo-1H-pyrrolo[2,3-b]pyridin-3-yl)-5-methylnicotinamide;
(R)—N-(4-(3-aminopiperidin-1-yl)-5-bromo-1H-pyrrolo[2,3-b]pyridin-3-yl)cyclopropane carboxamide;
(R)—N-(4-(3-aminopiperidin-1-yl)-5-bromo-1H-pyrrolo[2,3-b]pyridin-3-yl)-3-methylbutanamide; or
(R)—N-(4-(3-aminopiperidin-1-yl)-5-bromo-1H-pyrrolo[2,3-b]pyridin-3-yl)-2-cyclopropylacetamide.

In some working examples, CHK1 inhibitors used in the present method are (S)-5-(3-Fluorophenyl)-N-(piperidin-3-yl)-3-ureidothiophene-2-carboxamide;
Prexasertib; and
(R)-2-amino-2-cyclohexyl-N-(2-(1-methyl-1H-pyrazol-4-yl)-6-oxo-5,6-dihydro-1H-[1,2]diazepino[4,5,6-cd]indol-8-yl)acetamide.

Examples of PI3K inhibitors suitable for use in the present method include, but are not limited to,
(2S)-N1-[5-(2-tert-butyl-4-thiazolyl)-4-methyl-2-thiazolyl]pyrrolidine-1,2-dicarboxamide (A66);
(Z)-5-((5-(4-fluoro-2-hydroxyphenyl)furan-2-yl)methylene)thiazolidine-2,4-dione (AS-252424);
5-(2,2-Difluoro-benzo[1,3]dioxol-5-ylmethylene)-thiazolidine-2,4-dione (AS-604850);
(R)-2-(1-(7-methyl-2-morpholino-4-oxo-4H-pyrido[1,2-a]pyrimidin-9-yl)ethylamino)benzoic acid (AZD6482);
2-amino-N-[7-methoxy-8-(3-morpholinopropoxy)-2,3-dihydroimidazo[1,2-c]quinazolin (BAY 80-6945);
Copanlisib (BAY 80-6946);
8-(6-methoxypyridin-3-yl)-3-methyl-1-(4-(piperazin-1-yl)-3-(trifluoromethyl)phenyl)-1H-imidazo[4,5-c]quinolin-2(3H)-one maleate (BGT226);
Buparlisib (BKM120);
Alpelisib (BYL719);
(5E)-5-{[5-(4-fluorophenyl)furan-2-yl]methylidene}-1,3-thiazolidine-2,4-dione (CAY10505);
5-(2-Amino-8-fluoro-[1,2,4]triazolo[1,5-a]pyridin-6-yl)-N-tert-butylpyridine-3-sulfonamide (CZC24832);
Duvelisib (IPI-145);
2-((6-amino-9H-purin-9-yl)methyl)-5-methyl-3-o-tolylquinazolin-4(3H)-one (IC-87114);
Idelalisib (GS-1101, CAL-101);
Serabelisib (INK 1117);
Taselisib (GDC-0032);
Pictilisib (GDC-0941);
Apitolisib (GDC-0980);
(Z)-5-((4-(pyridin-4-yl)quinolin-6-yl)methylene)thiazolidine-2,4-dione (GSK1059615);
Omipalisib (GSK2126458);
2-methyl-1-(2-methyl-3-(trifluoromethyl)benzyl)-6-morpholino-1H-benzo[d]imidazole-4-carboxylic acid (GSK2636771);
6-[5-[(phenylsulfonyl)amino]-3-pyridinyl]-imidazo[1,2-a]pyridine-3-carboxylic acid, ethyl ester (HS-173);
2-amino-N,N-dimethyl-5-(3-(2-methylpyridin-4-yl)-1H-pyrrolo[2,3-b]pyridine-5-yl)pyridine-3-sulfonamide (HS-527);
2-(4-Morpholinyl)-8-phenyl-4H-1-benzopyran-4-one (LY294002);
Dactolisib (NVP-BEZ235);
Perifosine;
2-Amino-8-[4-(2-hydroxyethoxy)cyclohexyl]-6-(6-methoxypyridin-3-yl)-4-methylpyrido[2,3-d]pyrimidin-7-one (PF-04691502);
Gedatolisib (PF-05212384);
3-(4-morpholinopyrido[3',2':4,5]furo[3,2-d]pyrimidin-2-yl)phenol (PI-103);
2-methyl-5-nitro-2-[(6-bromoimidazo[1,2-a]pyridin-3-yl)methylene]-1-methylhydrazide-benzenesulfonic acid (PIK-75);
N-(2,3-dihydro-7,8-dimethoxyimidazo[1,2-c]quinazolin-5-yl)-3-pyridinecarboxamide (PIK-90);
2-[(4-amino-1H-pyrazolo[3,4-d]pyrimidin-1-yl)methyl]-5-methyl-3-(2-methylphenyl)-4 (3H)-quinazolinone (PIK-293);
2-[[4-amino-3-(3-hydroxyphenyl)-1H-pyrazolo[3,4-d]pyrimidin-1-yl]methyl]-5-methyl-3-(2-methylphenyl)-4 (3H)-quinazolinone (PIK-294);
1-(4-(3-ethyl-7-morpholino-3H-[1,2,3]triazolo[4,5-d]pyrimidin-5-yl)phenyl)-3-(4-(4-methylpiperazine-1-carbonyl)phenyl)urea (PKI-402);
Sonolisib (PX-866);
(S)-2-(2-(2-Methylindolin-1-yl)-2-oxoethyl)-6-morpholinopyrimidin-4(3H)-one (SAR260301);
Pilaralisib (SAR245408);
(2S)-2-[[(2S)-3-Carboxy-2-[[2-[[(2S)-5-(diaminomethylideneamino)-2-[[4-oxo-4-[[4-(4-oxo-8-phenylchromen-2-yl)morpholin-4-ium-4-yl]methoxy]butanoyl]amino]pentanoyl]amino]acetyl]amino]propanoyl]amino]-3-hydroxypropanoate (SF1126);
3-(2,4-Diaminopteridin-6-yl)phenol (TG100713);
Umbralisib (TGR-1202);
5-(9-Isopropyl-8-methyl-2-morpholino-9H-purin-6-yl)pyrimidin-2-amine (VS-5584);
Voxtalisib (XL765); and
4,4'-(6-(2-(Difluoromethyl)-1H-benzo[d]imidazol-1-yl)-1,3,5-triazine-2,4-diyl)dimorph oline (ZSTK474).

In some working examples, PI3K inhibitors used in the present method are Alpelisib;
Pictilisib; and
(Z)-5-((4-(pyridin-4-yl)quinolin-6-yl)methylene)thiazolidine-2,4-dione.

According to some embodiments of the present disclosure, the OSCC subject is treated with a CHK1 inhibitor when the ratio of CHEK1 gene between the lesion and the normal sites is at least 1.7. In the case when the ratio of the CHEK1 gene is less than 1.7, then a treatment other than the CHK1 inhibitor (e.g., surgery, radiotherapy, chemotherapy, immunotherapy, or a combination thereof) is administered to the OSCC subject. Alternatively or in addition, the OSCC subject is treated with a PI3K inhibitor when the ratio of PIK3CA gene or PIK3CD gene between the lesion and the normal sites is at least 2.4 or 3.1, respectively. In the case when the ratio of the PIK3CA gene or PIK3CD gene is less than 2.4 or 3.1, respectively, then a treatment other than the PI3K inhibitor is administered to the OSCC subject. In some embodiments, the OSCC subject with the ratio of CHEK1 at least 1.7 alone may exhibit a good response to a combination therapy of a CHK1 inhibitor (e.g., PF477736) plus a chemotherapeutic agent (e.g., Cisplatin). In other embodiments, the OSCC subject with the ratio of CHEK1 at least 1.7, and that of PIK3CA and/or PIK3CD at least 2.4 and/or 3.1, respectively, may exhibit a good response to a combination therapy of a CHK1 inhibitor (e.g., PF477736 or AZD7762) plus a PI3K inhibitor (e.g., BYL719 or GDC-0941).

Alternatively or optionally, the present method further comprises, prior to, in conjunction with, or subsequent to the treatment step described above (i.e., the step (d)), administering to the subject an additional anti-cancer treatment, such as surgery, radiotherapy, chemotherapy, immunotherapy, or a combination thereof. A combination therapy refers to a combination of at least two of the anti-cancer treatments listed above, for example, a combination of surgery and radiotherapy, a combination of surgery and chemotherapy and etc.

The chemotherapy is conducted by administering to a subject in need a chemotherapeutic agent to alleviate or ameliorate symptoms of the cancer. Examples of chemotherapeutic agent suitable for use in the present method include, but are not limited to, an alkylating agent, a platinum drug, an anti-metabolite, an anti-tumor antibiotic, a topoisomerase inhibitor, a mitotic inhibitor, and or an enzyme inhibitor. Exemplary alkylating agents include, but are not limited to, Chlormethine, Ifosfamide, Trofosfamide, Melphalan, Prednimustine, Bendamustine, Uramustine, Carmustine, Semustine, Fotemustine, Nimustine, Ranimustine, Streptozocin, Mannosulfan, Treosulfan, Carboquone, Thiotepa, Triaziquone, and Triethylenemelamine. Examples of the platinum drugs suitable for use in the present method are Carboplatin, Cisplatin, Dicycloplatin, Nedaplatin, Oxaliplatin, or Satraplatin.

In some embodiments, the chemotherapeutic agent used in the present method is the anti-metabolite, such as Aminopterin, Hydroxyurea, Methotrexate, Pemetrexed, Pralatrexate, Raltitrexed, Pentostatin, Cladribine, Clofarabine, Fludarabine, Nelarabine, Tioguanine, Mercaptopurine, Fluorouracil, Capecitabine, Doxifluridine, Tegafur, Carmofur, Floxuridine, Cytarabine, Gemcitabine, Azacitidine, Decitabine, or Hydroxycarbamide. The anti-tumor antibiotic may be Aclarubicin, Daunorubicin, Doxorubicin, Epirubicin, Idarubicin, Actinomycin, Bleomycin, Dactinomycin, Mitomycin, or Plicamycin. Also, the topoisomerase inhibitor may be Camptothecin, Cositecan, Belotecan, Gimatecan, Exatecan, Irinotecan, Lurtotecan, Silatecan, Topotecan, Rubitecan, Etoposide, or Teniposide.

In addition, the mitotic inhibitor suitable for use in the present method is Vinblastine, Vincristine, Vinflunine, Vindesine, Vinorelbine, Cabazitaxel, Docetaxel, Larotaxel, Ortataxel, Paclitaxel, Tesetaxel, or Ixabepilone. Furthermore, the enzyme inhibitor may be Tipifarnib, Abemaciclib, Alvocidib, Palbociclib, Ribociclib, Seliciclib, Bortezomib, Carfilzomib, Ixazomib, Anagrelide, Tiazofurin, Masoprocol, Niraparib, Olaparib, Rucaparib, Belinostat, Panobinostat, Romidepsin, Vorinostat, or Idelalisib.

According to some embodiments of the present disclosure, the chemotherapeutic agent as used herein may be Bleomycin, Carboplatin, Capecitabine, Cisplatin, Docetaxel, 5-FU, Hydroxyurea, Methotrexate, and Paclitaxel. In one working example of the present disclosure, the chemotherapeutic agent is Cisplatin.

Immunotherapy refers to killing cancer cells by one's own immune system. More specifically, by activating the patient's own immune system so that it attacks the malignant cells that are responsible for the disease. In some embodiments, immunotherapy is associated with the use of immune checkpoint inhibitors as immunotherapeutic agents to treat cancers. Exemplary immunotherapeutic agents include, but are not limited to, Pembrolizumab, Nivolumab, Cemiplimab, Spartalizumab, Camrelizumab, Sintilimab, Tislelizumab, Toripalimab, Nivolumab, Atezolizumab, Avelumab, Durvalumab, and Ipilimumab.

The effective amount of the therapeutic agent (e.g., CHK1 inhibitor, PI3K inhibitor, chemotherapeutic agent, and the like) in the present method may vary with many factors, such as the particular condition being treated, the severity of the condition, the individual patient parameters (including age, physical condition, size, gender and weight), the duration of the treatment, the nature of concurrent therapy (if any), the specific route of administration and like factors within the knowledge and expertise of the health practitioner.

To elicit a therapeutic effect in human, the therapeutic agent (e.g., CHK1 inhibitor, PI3K inhibitor, chemotherapeutic agent, and the like) in the present method is administered to the subject in a dose about 10 µg/kg to 50 mg/kg (e.g., 10, 20, 30, 40, 50, 60, 70, 80, 90, 100, 150, 200, 250, 300, 350, 400, 450, 500, 550, 600, 650, 700, 750, 800, 850, 900, or 950 µg/kg, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 mg/kg) body weight; preferably, the therapeutic agent in the present method is administered to the subject in a dose about 50 µg/kg to 10 mg/kg body weight; more preferably, the therapeutic agent in the present method is administered to the subject in a dose about 0.5 mg/kg to 5 mg/kg body weight. According to one working example, the therapeutic agent is the chemotherapeutic agent Cisplatin, and the dose is about 0.5 mg/kg body weight to elicit a therapeutic effect (e.g., reducing the volume of tumors) in the subject. According to another working example, the therapeutic agent is the CHK1 inhibitor PF477736, and the dose is about 1 or 2 mg/kg body weight to elicit a therapeutic effect in the subject. According to another working example, the therapeutic agent is the PI3K inhibitor BYL719, and the dose is about 2.5 or 5 mg/kg body weight to elicit a therapeutic effect in the subject.

The effective amount of a therapeutic agent (e.g., CHK1 inhibitor, PI3K inhibitor, chemotherapeutic agent, and the like) in the present method may be administered in a single dose (e.g., single intraperitoneal injection dose) or multiple doses (e.g., multiple intraperitoneal injection doses). In certain embodiments, when multiple doses are administered to a subject, the frequency of administering the multiple doses to the subject is three doses a day, two doses a day, one dose a day, five doses every week, four doses every week, three doses every week, two doses every week, one dose every week, one dose every other week, one dose monthly or one dose every other month. In certain embodiments, the frequency of administering the multiple doses to the subject is five doses every week. In certain embodiments, the frequency of administering the multiple doses to the subject is four doses every week. In certain embodiments, the frequency of administering the multiple doses to the subject is two doses every week.

In certain embodiments, when multiple doses are administered to a subject, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject. In certain embodiments, the duration between the first dose and last dose of the multiple doses is three months, six months, or one year. In certain embodiments, the duration between the first dose and last dose of the multiple doses is the lifetime of the subject. In a specific embodiment, the duration between the first dose and last dose of the multiple doses is four weeks.

In the present methods, the therapeutic agent suitable for use in the present method may be administered via routes known to those skilled in the art, including oral, intracranial, intraspinal, intrathecal, intramedullar, intracerebral, intracerebroventricular, intravenous, intraarterial, intracardial, intracutaneous, subcutaneous, transdermal, intraperitoneal, and intramuscular route.

As would be appreciated, a method for predicting a likelihood that a subject with an oral cancer will exhibit a beneficial response to a checkpoint kinase 1 inhibitor, or a phosphatidylinositol 3-kinase inhibitor is also encompassed in the present disclosure. The method comprises, (a) respectively measuring the expression levels of a biomarker in a first and a second samples obtained from the subject by qRT-PCR thereby obtaining a first expression level and a second expression level of the biomarker, wherein the biomarker is CHEK1 gene, PIK3CA gene, or PIK3CD gene, and the first and second samples are respectively a cancerous sample and a non-cancerous sample;

(b) determining the ratio of the first expression level to the second expression level; and (c) determining the likelihood that the subject will exhibit a beneficial response to a checkpoint kinase 1 inhibitor or a phosphatidylinositol 3-kinase inhibitor based on the ratio determined in the step (b), wherein:

the subject is likely to exhibit a beneficial response to the checkpoint kinase 1 inhibitor in the case when the biomarker is the CHEK1 gene, and the ratio is at least 1.7, or the phosphatidylinositol 3-kinase inhibitor in the case when the biomarker is the PIK3CA gene, and the ratio is at least 2.4; or when the biomarker is the PIK3CD gene, and the ratio determined in the step (c) is at least 3.1.

As would be appreciated, a kit for detecting a subject with an oral cancer will response to a kinase inhibitor is also encompassed in the present disclosure. The kit comprises a primer pair of SEQ ID NO: 1 and 2, SEQ ID NO: 3 and 4, or SEQ ID NO: 5 and 6; wherein, the primer pair of SEQ ID NO: 1 and 2 is used for detecting the expression level of CHEK1 gene; the primer pair of SEQ ID NO: 3 and 4 is used for detecting the expression level of PIK3CA gene; the primer pair of SEQ ID NO: 5 and 6 is used for detecting the expression level of PIK3CD gene; and the kinase inhibitor is selected from the group consisting of checkpoint kinase 1 inhibitor or a phosphatidylinositol 3-kinase inhibitor. Alternatively, the kit further comprises a primer pair of SEQ ID NO: 7 and 8, in which the primer pair of SEQ ID NO: 7 and 8 is used for detecting the expression level of TBP gene.

The following Examples are provided to elucidate certain aspects of the present invention and to aid those of skilled in the art in practicing this invention. These Examples are in no way to be considered to limit the scope of the invention in any manner. Without further elaboration, it is believed that one skilled in the art can, based on the description herein, utilize the present invention to its fullest extent. All publications cited herein are hereby incorporated by reference in their entirety.

EXAMPLES

Materials and Methods

1. Patients and Clinical Specimens

One cohort of Taiwanese patients was enrolled in the present study which was approved by the Institutional Review Board at Chang Gung Memorial Hospital, Taiwan. A written informed consent was obtained for all participants before the sample collection was done. The cohort comprised 32 treatment-naive OSCC patients, whose clinical characteristics were provided in Table 1.

TABLE 1

Clinical characteristics of 32 OSCC patients

| Characteristics | OSCC (N = 32) | |
| --- | --- | --- |
| | STAGE 1 & 2 | STAGE 3 & 4 |
| Number of patients | 5 | 27 |
| Age (years) | | |
| range | 44~85 | 35~66 |
| mean ± SD | 60.2 ± 15.0 | 50.8 ± 9.1 |
| Gender | | |
| Male | 4 (80.0%) | 25 (92.6%) |
| Female | 1 (20.0%) | 2 (7.4%) |
| T stage | | |
| T1, 2 | 5 (100.0%) | 11 (40.7%) |
| T3, 4 | 0 (0.0%) | 16 (59.3%) |
| N stage | | |
| N(−) | 5 (100.0%) | 4 (14.8%) |
| N(+) | 0 (0.0%) | 23 (85.2%) |
| Overall stage | | |
| I | 1 (20.0%) | — |
| II | 4 (80.0%) | — |
| III | — | 6 (22.2%) |
| IV | — | 21 (77.8%) |
| Alcohol drinking | | |
| NO | 2 (40.0%) | 5 (18.5%) |
| YES | 3 (60.0%) | 22 (81.5%) |
| Betel quid chewing | | |
| NO | 2 (40.0%) | 4 (14.8%) |
| YES | 3 (60.0%) | 23 (85.2%) |
| Cigarette smoking | | |
| NO | 2 (40.0%) | 4 (14.8%) |
| YES | 3 (60.0%) | 23 (85.2%) |

2. Cell Lines

OSCC cell lines, including SAS (ATCC® 64403™), OEC-M1 (CVCL_6782), and OC3 (CVCL_D859), were used in the present study. SAS cells were maintained in Dulbecco's modified Eagle's medium (DMEM; Gibco, USA) supplemented with 100 U/ml penicillin and 100 µg/ml streptomycin (Gibco, USA), and 10% fetal bovine serum (FBS; Gibco, USA). OEC-M1 cells were maintained in Roswell Park Memorial Institute 1640 medium (RPMI 1640; Thermo Fisher Scientific, USA), and OC3 cells were maintained in DMEM (Gibco, USA) with keratinocyte serum-free medium (KSFM; Gibco, USA); both were supplemented with 10,000 U/ml penicillin and 10,000 µg/ml streptomycin (Gibco, USA), and 10% FBS (Gibco, USA). All cell lines were maintained at 37° C. in a humidified atmosphere containing 5% $CO_2$.

3. Drugs, Chemicals, and Antibodies

CHK1 inhibitors PF477736 (Sigma-Aldrich, USA), AZD7762 (Selleck Chemicals, CA), and LY2606368 (MedChem Express, USA); as well as PI3K inhibitors GDC-0941 (Cayman Chemical, USA) GSK1059615 (Cayman Chemical, USA), and BYL719 (Novartis Pharma AG, Basal, Switzerland) were dissolved in dimethyl sulfoxide (DMSO; Sigma-Aldrich, USA), and stored at −20° C. Cisplatin (Sigma-Aldrich, USA) was dissolved in 1×PBS, and stored at 4° C. All antibodies used in the immunoblotting assay were: anti-CHK1, anti-p-CHK1-Ser296, anti-AKT, anti-p-AKT-Ser473, anti-Ki-67 (Cell Signaling Technology); anti-GAPDH (Bioworlde, USA); HRP-conjugated goat-anti-rabbit IgG (PerkinElmer, USA); and HRP-conjugated goat-anti-mouse IgG (PerkinElmer, USA).

4. RNA Extraction and qRT-PCR

Total RNA from the paired OSCC tumor tissues and surrounding normal tissues was extracted using TRIzol Reagent (Gibco BRL), and the quality and quantity was confirmed using an Agilent 2100 Bioanalyzer (Agilent Technologies, Santa Clara, Calif.). For qRT-PCR, first-strand complementary DNA was synthesized from 1 μg of total RNA using random hexamers (GeneDirex, Germany) and SuperScript III RT (Invitrogen, USA), and qRT-PCR analysis was carried out using MicroAmp Fast 96-Well Reaction Plate (0.1 mL) (Applied Biosystems, USA). The primers utilized in qRT-PCR were listed in Table 2. A mean cycle threshold (Ct) value for each duplicate measurement was calculated. To determine the normalized value, $2^{-\Delta Ct}$ values of tumor tissues and adjacent normal tissues were compared. $\Delta Ct = Ct_{Target} - Ct_{TBP}$.

TABLE 2

Primers for qRT-PCR

| Name | Sequence | SEQ ID NO |
|---|---|---|
| CHEK1-F | TCGGTATAATAATCGTGAGCG | 1 |
| CHEK1-R | ACAGGACCAAACATCAACTG | 2 |
| PIK3CA-F | ACGATGGACAACTGTTTCA | 3 |
| PIK3CA-R | GTCTTTGTGCATTCTTGGG | 4 |
| PIK3CD-F | GACATCCAGTATCTCAAGGAC | 5 |
| PIK3CD-R | AGCCAGTTCACTTTGGTT | 6 |
| TBP-F849 | TGCTCACCCCACCAACAATTTAG | 7 |
| TBP-R969 | CTGGGTTTGATCATTCTGTAGATTAA | 8 |

5. Cell Viability Assay

For cell viability assay, approximately $5 \times 10^4$ cells were seeded into each well of a 96-well plate, and treated with vehicle control or inhibitors at the indicated concentrations for 48 hours in complete medium, followed by MTT viability assay. The absorbance was read at 540 nm in a multiwell spectrophotometer (SpectraMax M2; Molecular Devices, USA). All samples were run in triplicate. For apoptosis assay, cells were plated in 6-well dishes, and treated with vehicle control or various inhibitors at the indicated concentrations for 48 hours. Cells were then harvested, washed with PBS, and stained with 2 μl an FITC-conjugated Annexin V antibody (Invitrogen, USA) and 50 μg/ml propidium iodide (Sigma-Aldrich, USA), followed by flow cytometry analysis (Attune NxT; Invitrogen, USA) and data analysis by FlowJo software (Tree Star, Inc.).

6. Immunoblotting

After treatments, whole-cell lysates from each sample were prepared by lysed with RIPA lysis buffer (1% NP—40, 20 mM Tris-HCl (pH 7.5), 150 mM NaCl, 1 mM Na3VO4, 5 mM EDTA (pH 8.0), 10% glycerol, PMSF, and 0.2% protease inhibitor) for 15-30 minutes on ice, and centrifuged at 15,000×g for 20 min at 4° C. Equal amounts of protein from each sample were fractionated by SDS-PAGE, and transferred to a PVDF membrane, which was incubated with the appropriate primary antibody. Proteins were detected with HRP-conjugated secondary antibodies and ECL substrate (PerkinElmer, USA).

7. Immunohistochemistry Staining

Immunohistochemical staining was performed using an immunohistochemistry staining instrument (Bond, Leica BioSystems). Tissue sections were retrieved using the Bond-max automated immunostainer (Leica BioSystems), and stained with anti-Ki-67 antibody (mouse monoclonal antibody to Ki-67, Cell Signaling). A polymer detection system (Bond Polymer Refine Detection, Leia BioSystems) was used to reduce nonspecific staining. Tissue sections were treated with 3,3'-diaminobenzidine reagent as a chromogen, and hematoxylin as counterstain.

8. Animal Experiments

NOD/SCID mice and NOD.Cg-Prkdcscid Il2rgtm1Wjl/SzJ (NSG) mice were housed in an animal facility at Chang Gung University. For SAS cell line-derived xenograft (CDX) animal model, SAS cells were prepared in serum-free DMEM ($5 \times 10^6$ cells per ml). SAS cell suspensions (100 μl) were injected subcutaneously into NOD/SCID mice (6-8 weeks), and tumors were established after 3-4 weeks. Once xenografts reached 300-500 mm³, mice were randomly divided into the treatment groups or control groups. PF477736 was used at the dose of 10 or 20 mg/kg, and administered intraperitoneally 4 days/week. BYL719 was used at the dose of 25 or 50 mg/kg, and administered orally 5 days/week. Cisplatin was used at the dose of 5 mg/kg, and administered intraperitoneally 2 days/week. During the course of treatment (two to three weeks), the tumor size was monitored twice weekly, and the tumor volumes were calculated.

For OSCC PDX animal model, three patients of newly diagnosed were recruited, and written consents were obtained in accordance with the protocols approved by the Institutional Review Board of Chang Gung Memorial Hospital. Patient tumor explants were prepared from surgical specimens, and engrafted into NSG mice within 2 hours. Briefly, fresh tumor tissues were rinsed in PBS containing an antibiotic-antimycotic solution (Gibco, USA), and chopped into small pieces (~1 mm³). Each NSG mouse was subcutaneously grafted with 50-100 mg tumors in the left flank. When tumors reached 400-500 mm³ in size, animals were randomly assigned into control and different treatment groups. Treatments for each single drug were the same as those used in the SAS CDX model as described above. For combined treatments, for the combination therapy of Cisplatin and PF477736, Cisplatin was used at the dose of 5 mg/kg, and administered intraperitoneally 2 days/week for one week; whilst PF477736 was used at the dose of 20 mg/kg, and administered intraperitoneally 4 days/week for one week; and for the combination therapy of PF477736 and BYL719, PF477736 was used at the dose of 20 mg/kg, and administered intraperitoneally 4 days/week for one week; whilst BYL719 was used at the dose of 50 mg/kg, and administered orally 5 days/week for two weeks. Tumors were measured with calipers, and the volume was calculated as ½×length×width². Three PDX models in total were evaluated for response to single treatments or combined treatments. All animal experiments were approved by the Institutional Animal Care and Use Committee of Chang Gung University.

9. Statistical Analysis

Patient characteristics were stratified by various clinicopathological factors, and calculated by the chi-square test. All statistical data are expressed as the mean S.E.M. Between-group comparisons were performed by Student's t-test or Mann-Whitney U test for two groups. All statistical tests were performed using SPSS software version 12.0 (SPSS, Inc., Chicago, Ill, USA) or Prism. p value<0.05 was deemed statistically significant.

Example 1 Genes Differentially Expressed in OSCC

In order to understand genes that are differentially expressed in OSCC, a comprehensive transcriptome studying approach RNA-seq was deployed to analyze the matched tumor tissues and adjacent normal tissues from 32 OSCC patients (data not shown).

Figure 1B:
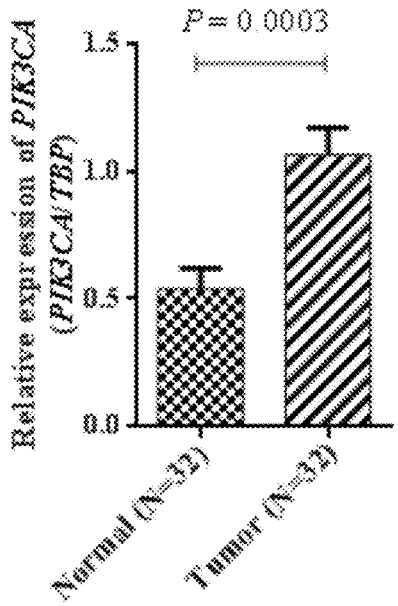
Figure 1C:
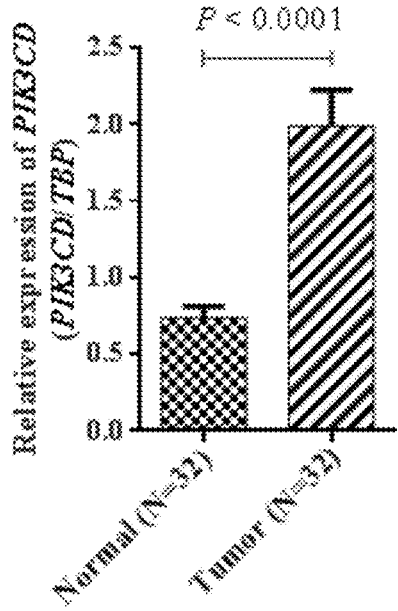
Figure 1D:
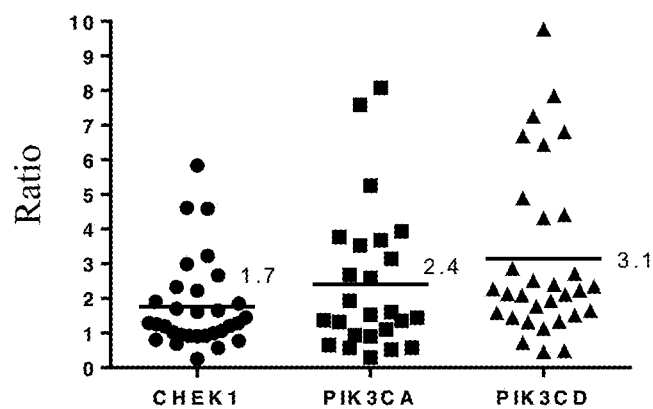

From the data obtained from the foregoing approaches, three genes: CHEK1, PIK3CA, and PIK3CD were found to be differentially expressed in OSCC. The expression of these genes in the 32 paired OSCC cohorts was further confirmed by qRT-PCR. As illustrated in FIG. 1A, CHEK1 expression was increased in OSCC as compared to the surrounding normal tissues. Similar results were found in PIK3CA and PIK3CD (FIGS. 1B-1C). The expression alteration of the genes in each paired OSCC sample was determined, and the thresholds to define highly expression were set, in which the threshold for CHEK1 was 1.7, for PIK3CA was 2.4, and for PIK3CD was 3.1 (FIG. 1D).

Taken together, these findings indicated that CHEK1, PIK3CA, and PIK3CD were significantly upregulated in OSCC patients.

Example 2 Effects of CHK1 and PI3K Inhibition on OSCC In Vitro and In Vivo

2.1 Effects of CHK1 Inhibition on OSCC In Vitro

Figure 2A:
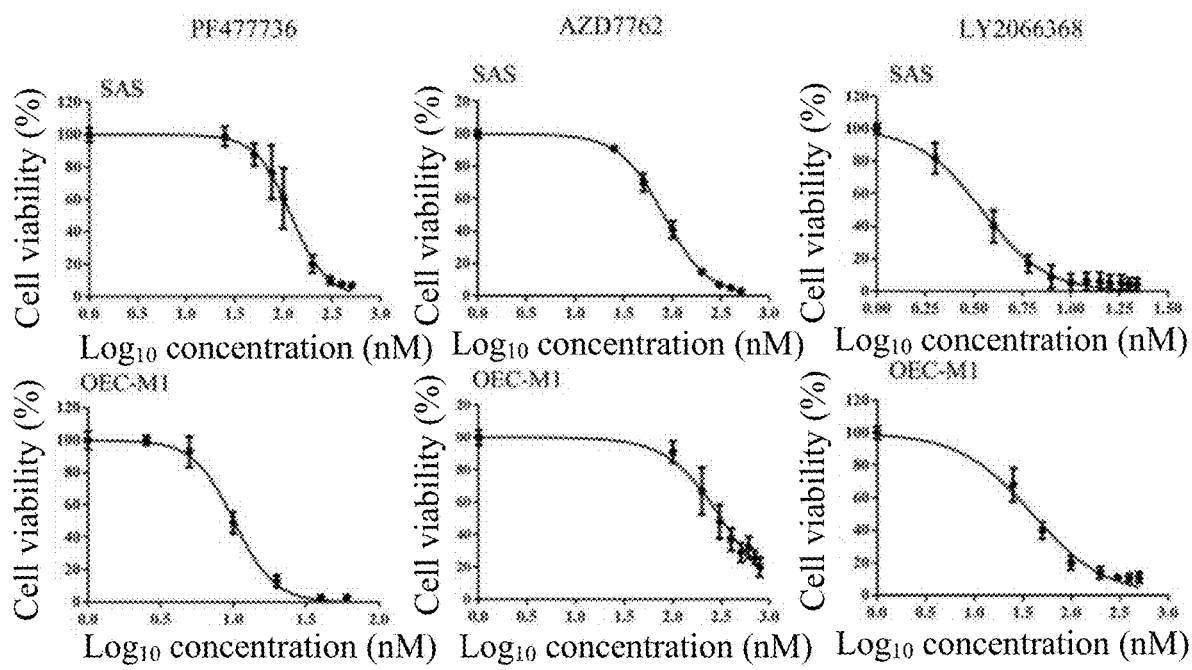
FIGS. 2A-2F depict the treatment effect of CHK1 inhibitor on OSCC.
Figure 2B:
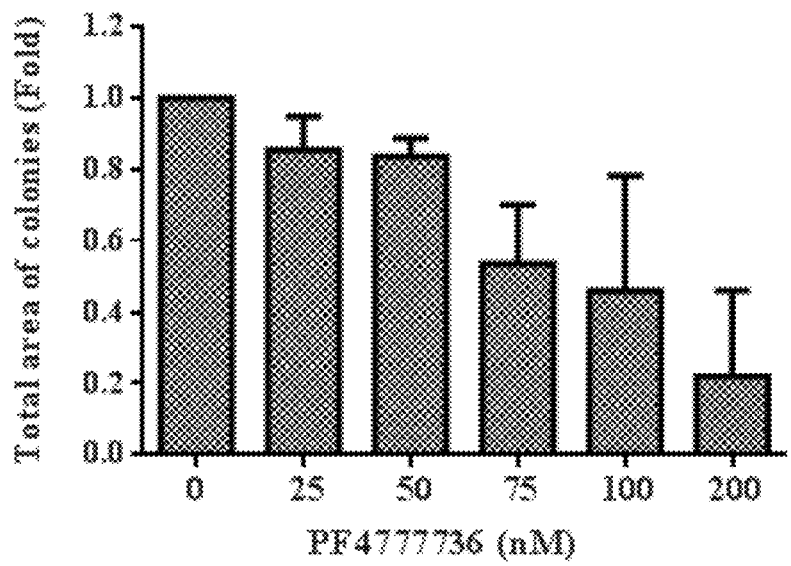
Figure 2B:
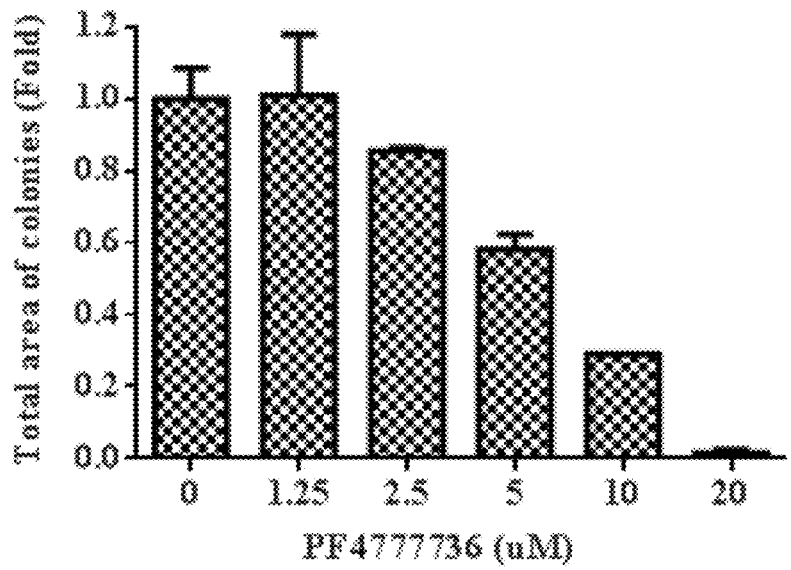
Figure 2C:
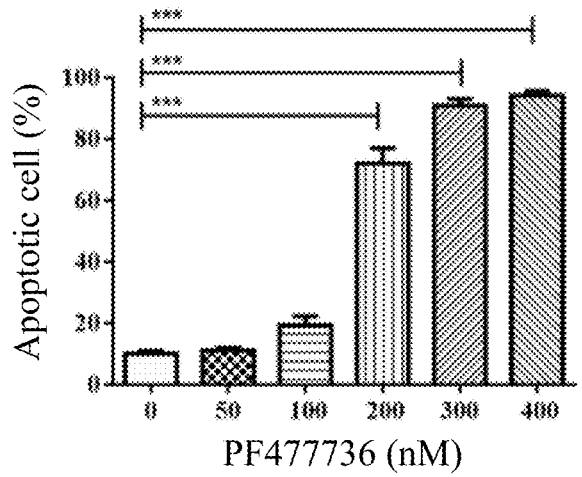
Figure 2C:
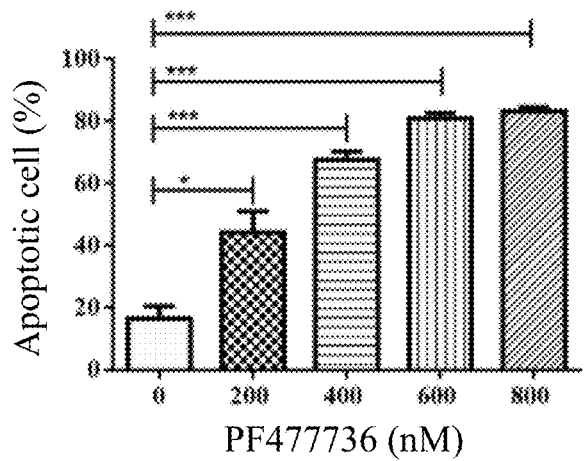
Figure 2C:
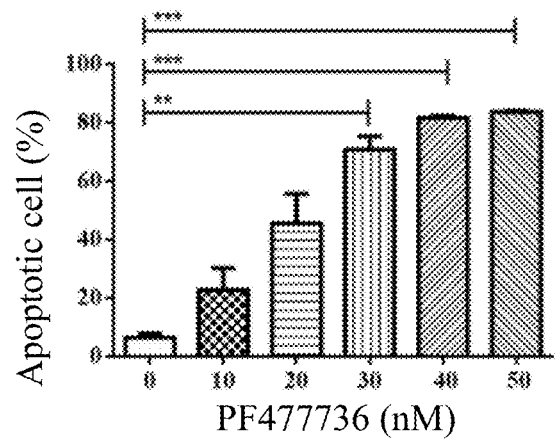
Figure 2D:
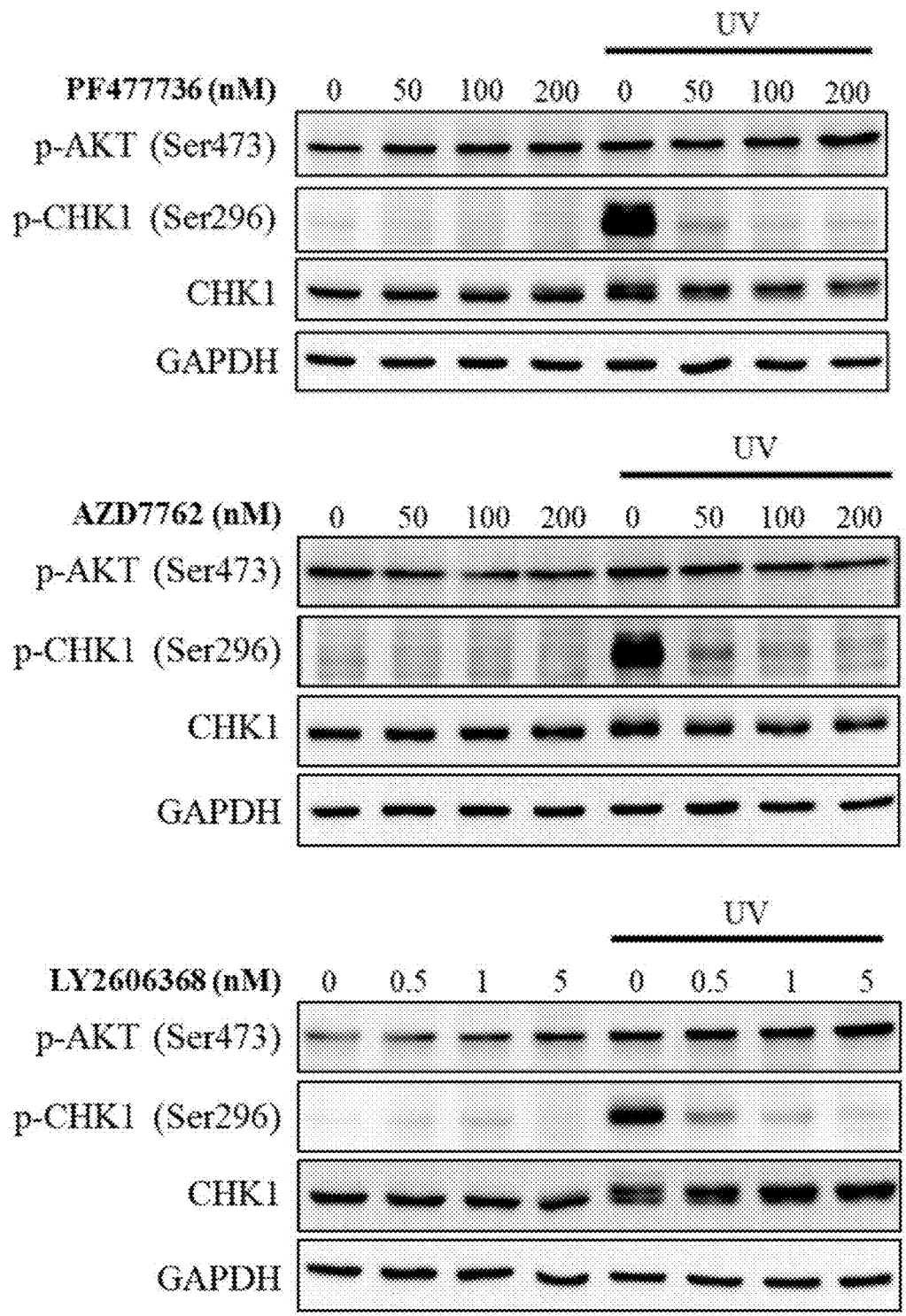

To evaluate the feasibility of inhibiting CHK1 and PI3K as an approach against tumors, several small molecule inhibitors of CHK1 and PI3K were tested in this Example. Results of specific CHK1 inhibitors (including PF477736, AZD7762, and LY2606368) on cell viability of OSCC cell lines (including SAS, and OEC-M1) were provided in FIG. 2A. All the CHK1 inhibitors tested exhibited dose-dependent inhibition on both SAS and OEC-M1 cells (FIG. 2A). The half-maximal inhibitory concentration ($IC_{50}$) for PF477736 in the SAS cells ranged from 120 to 400 nM, whereas the $IC_{50}$ concentration for OEC-M1 cells was 10 µM (FIG. 2A). In addition, the colony-forming ability of SAS and OEC-M1 cells after treated with PF477736 was examined, and results showed that PF477736 significantly impaired the colony-forming ability of both cells (FIG. 2B). Moreover, PF477736 significantly exacerbated cell apoptosis in three OSCC cells, including SAS, OC3, and OEC-M1 cells, as assessed by Annexin V and PI staining (FIG. 2C). On the molecular level, the biochemical effects of the three CHK1 inhibitors in SAS cells were characterized. DNA damage was first induced by UV exposure, and the CHK1 inhibitors were then applied to the injured cells. Afterwards, phosphorylation of CHK1 at Ser296 and total CHK1 were analyzed by immunoblotting (FIG. 2D). The results showed that the CHK1 inhibitors (i.e., PF477736, AZD7762, and LY2606368) were able to specifically reduce phosphorylation of CHK1 after UV exposure, suggesting that CHK1 activity was severely suppressed after CHK1 inhibitor treatments.

Figure 2E:
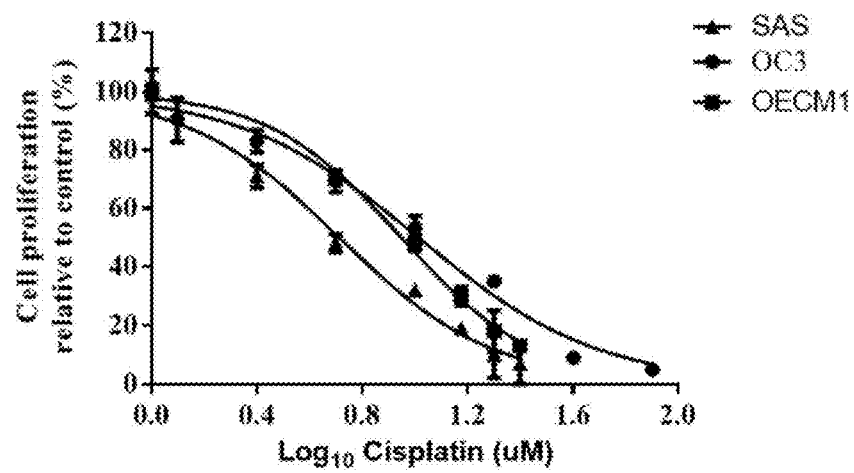
Figure 2F:
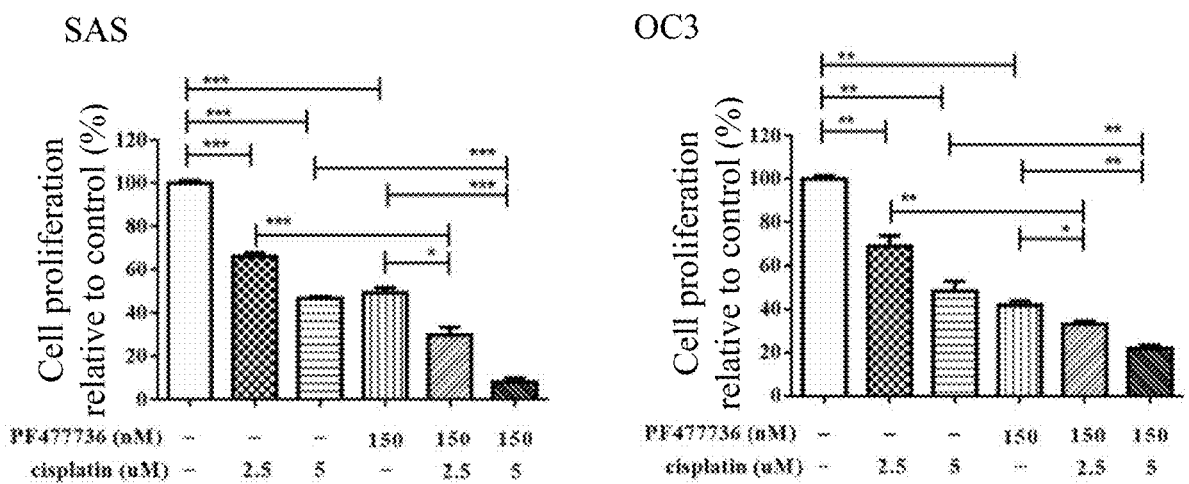

In order to evaluate the combination therapy with CHK1 inhibitors and a current standard chemotherapy in treating OSCC, PF477736 and Cisplatin were chosen as an example as the CHK1 inhibitor part and the chemotherapy part of the combination therapy in the present study, respectively. To start with, the $IC_{50}$ for Cisplatin in treating three OSCC cells (SAS, OC3, and OEC-M1 cells) was determined, ranging from 2.5 to 5 µM (FIG. 2E). Next, the efficacy of the combination therapy was evaluated by examining the ability to suppress cell proliferation. As provided in FIG. 2F, the combination treatment of PF477736 and Cisplatin synergistically hampered SAS and OC3 cell proliferation as compared with control or single-agent treatment.

Collectively, these results evidenced that CHK1 inhibitors alone or in combination with chemotherapy (e.g., Cisplatin) effectively slowed down cell proliferation, prompted cell cycle arrest, and triggered cell death in OSCC.

2.2 Effects of PI3K Inhibition on OSCC In Vitro

Figure 3A:
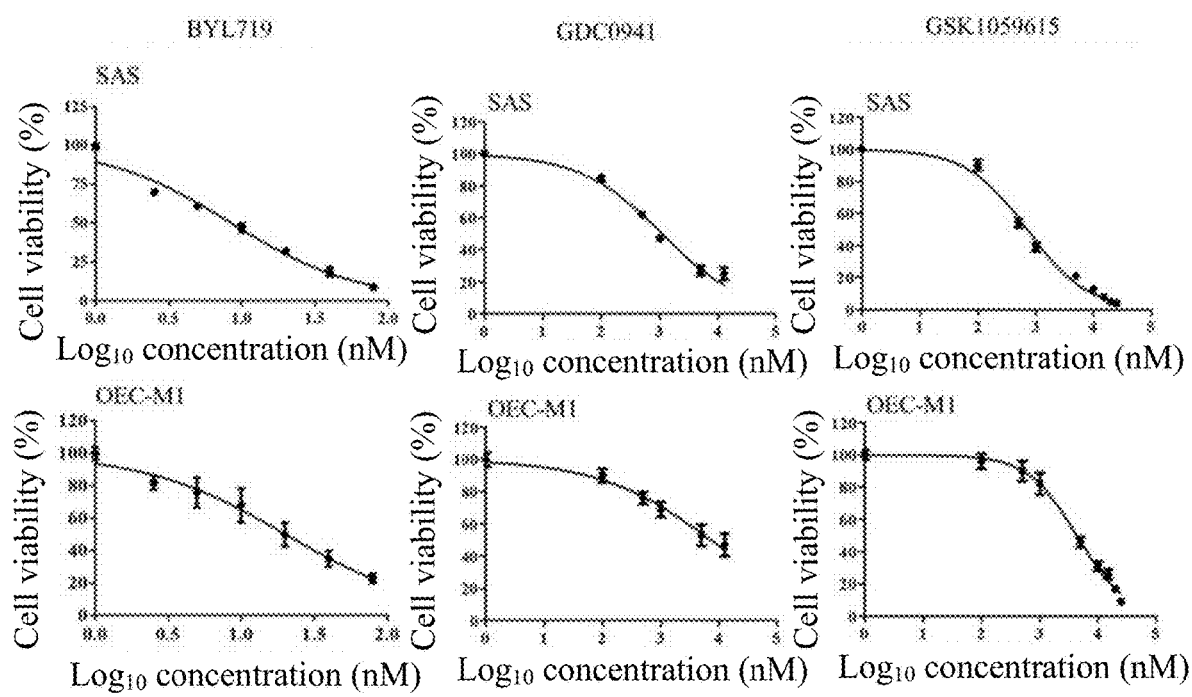
FIGS. 3A-3G depict the treatment effect of the PI3K inhibitor on OSCC.
Figure 3B:
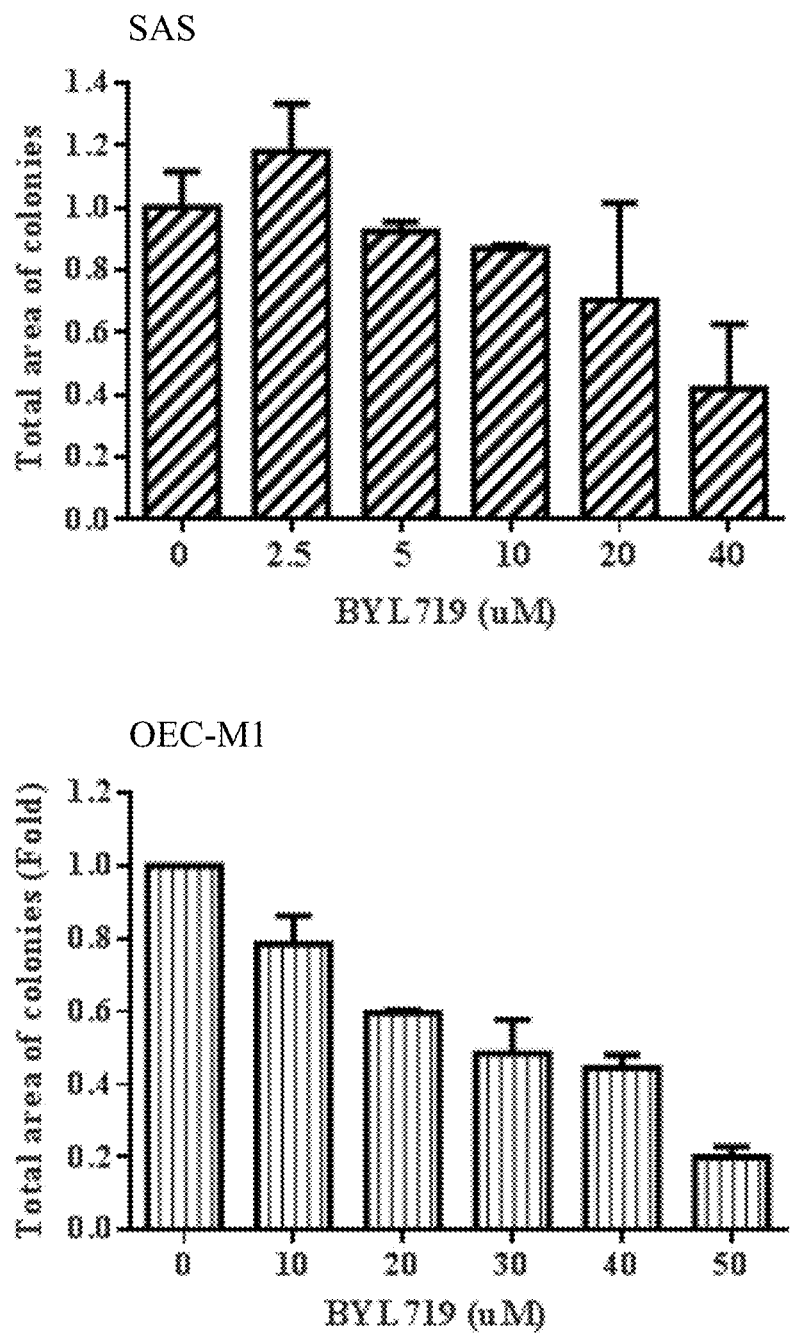
Figure 3C:
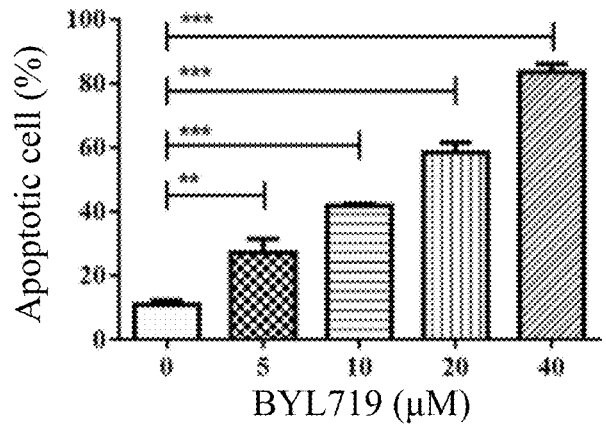
Figure 3C:
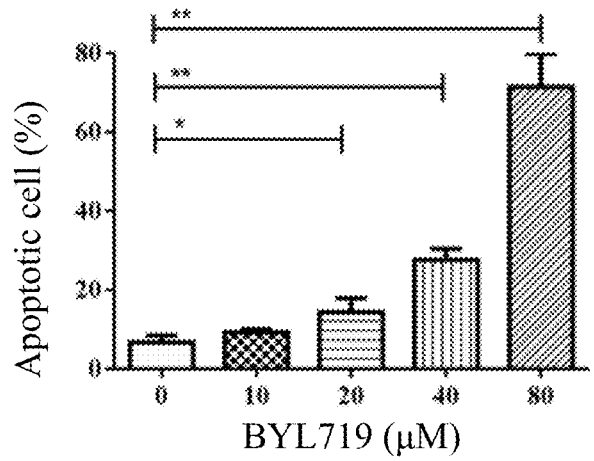
Figure 3C:
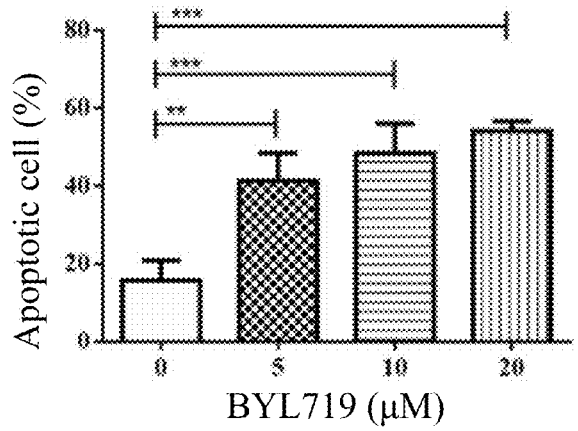
Figure 3D:
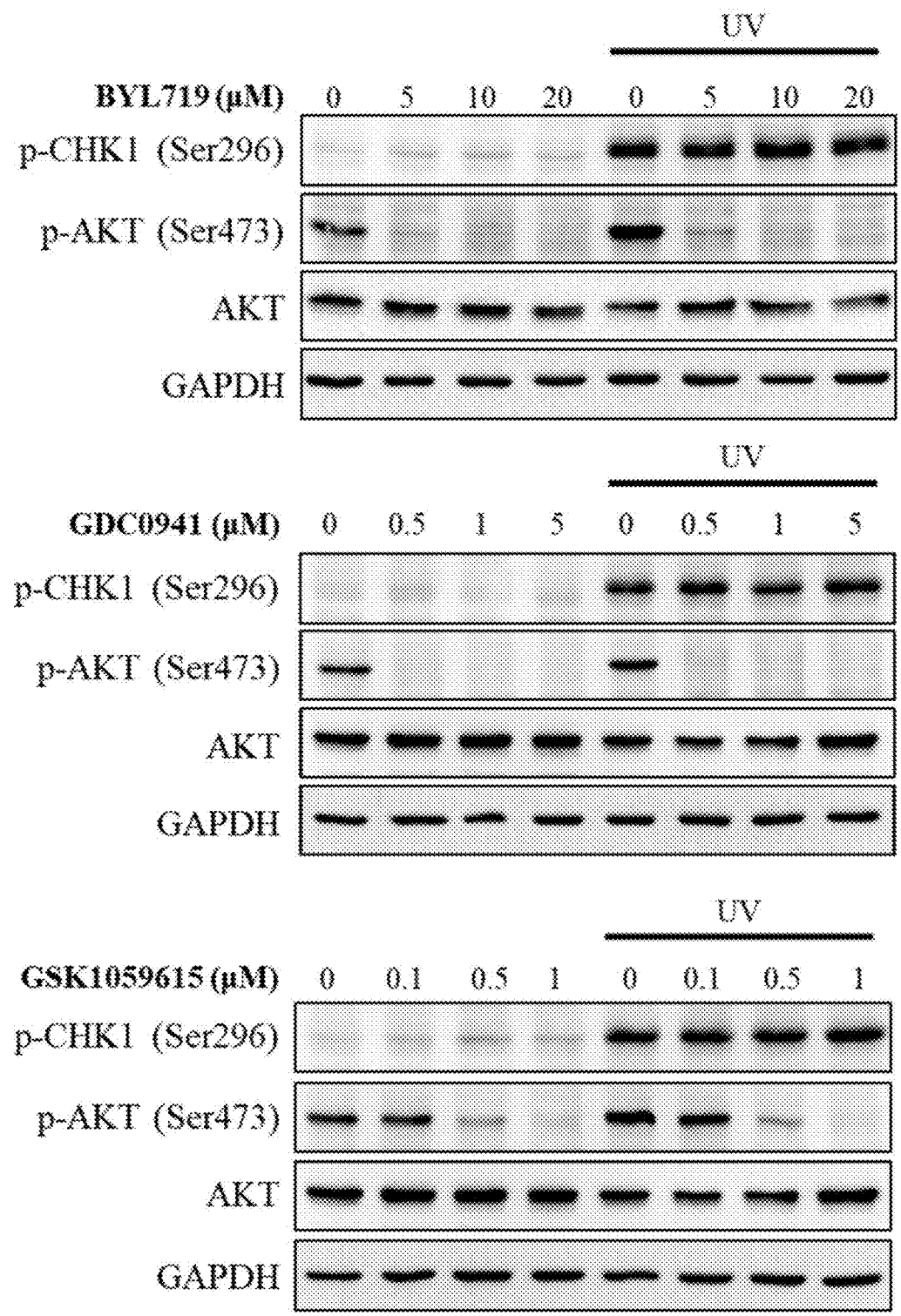

In the present study, the efficacy of the PI3K inhibitors (e.g., BYL719, GDC-0941, and GSK1059615) toward eliminating OSCC cell lines (including SAS, OEC-M1, and OC3) was examined. First of all, cell proliferation assays after the PI3K inhibitors (i.e., BYL719, GDC-0941, and GSK1059615) treatments were performed, and the results were provided in FIG. 3A. According to the results, SAS and OEC-M1 cells treated with PI3K inhibitors exhibited clear reduction in proliferation as compared with those treated with vehicle controls (FIG. 3A). The $IC_{50}$ for BYL719 in the SAS, OC3, and OECM1 cell lines ranged from 8 to 20 µM (FIG. 3A). Another indication for measuring anti-cancer activity was by investigating the colony-forming ability of SAS and OEC-M1 cells treated with BYL719. As shown in FIG. 3B, the colony-forming ability of the treated cells was compromised in a dose-dependent manner. As to cell apoptosis, OSCC cells treated with BYL719 showed gradually elevation in apoptosis along with incretion of BYL719 concentration (FIG. 3C). The effects for PI3K inhibitors on the PI3K/AKT/mTOR signaling pathway were studied as well. According to FIG. 3D, PI3K inhibitors (i.e., BYL719, GDC-0941, and GSK1059615) specifically inhibited phosphorylation of AKT after UV exposure, thereby blunting the PI3K/AKT/mTOR signaling pathway after treatments.

Figure 3E:
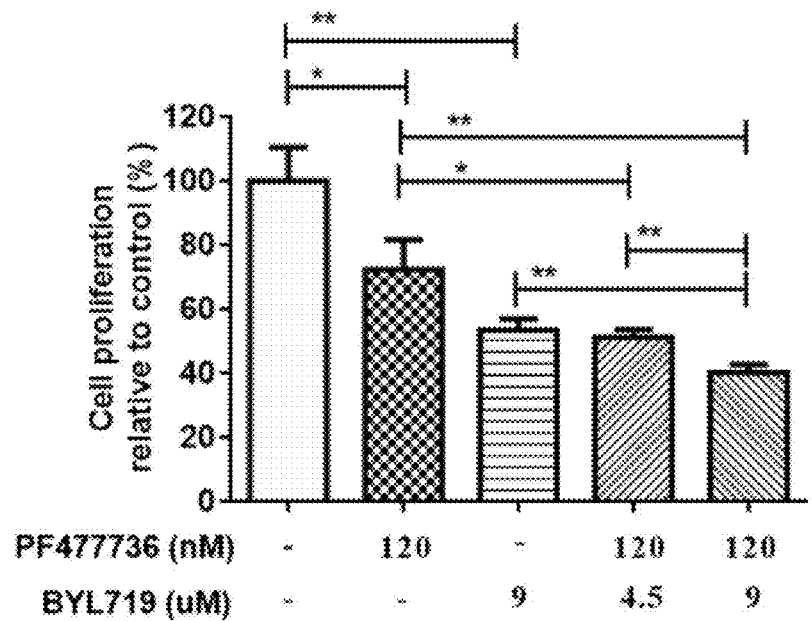
Figure 3F:
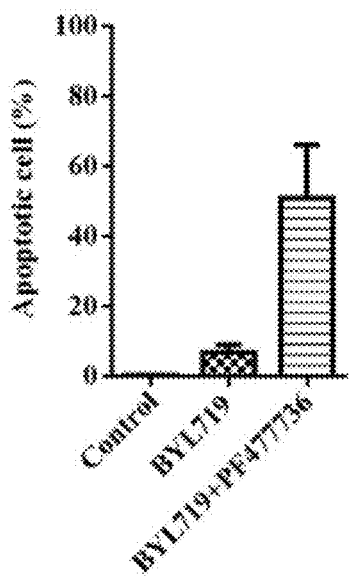
Figure 3G:
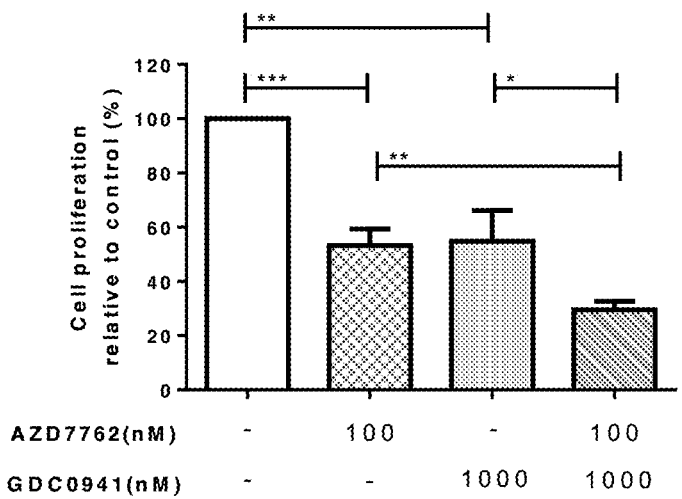

The efficacy of PI3K inhibitors in combination with CHK1 inhibitors as a combination therapy for treating cancers was evaluated in the present study. As an example, PF477736 and BYL719 were used as the CHK1 inhibitor and the PI3K inhibitor, respectively, in the following experiments. Results of cell proliferation after the combination therapy administered were provided in FIG. 3E, indicating that the combination treatments synergistically impeded proliferation in SAS cells as compared with control or single-agent treatment. In addition, the combination treatments significantly increased the amount of apoptotic cells in SAS cells (FIG. 3F). Similar results were found in suppression of cell proliferation using the combination therapy, in which the CHK1 inhibitor and the PI3K inhibitor were AZD7762 and GDC-0941, respectively (FIG. 3G).

In sum, these findings suggested that PI3K inhibitors have a good anti-cancer activity, and a combination therapy with PI3K and CHK1 inhibitors may aid in treating cancers.

2.3 Effects of Combination Therapy on OSCC In Vivo

The data as described above have prompted the inventors to further investigate the anti-tumor activities of the CHK1 and PI3K inhibitors alone or in combination in in vivo OSCC preclinical models.

Figure 4A:
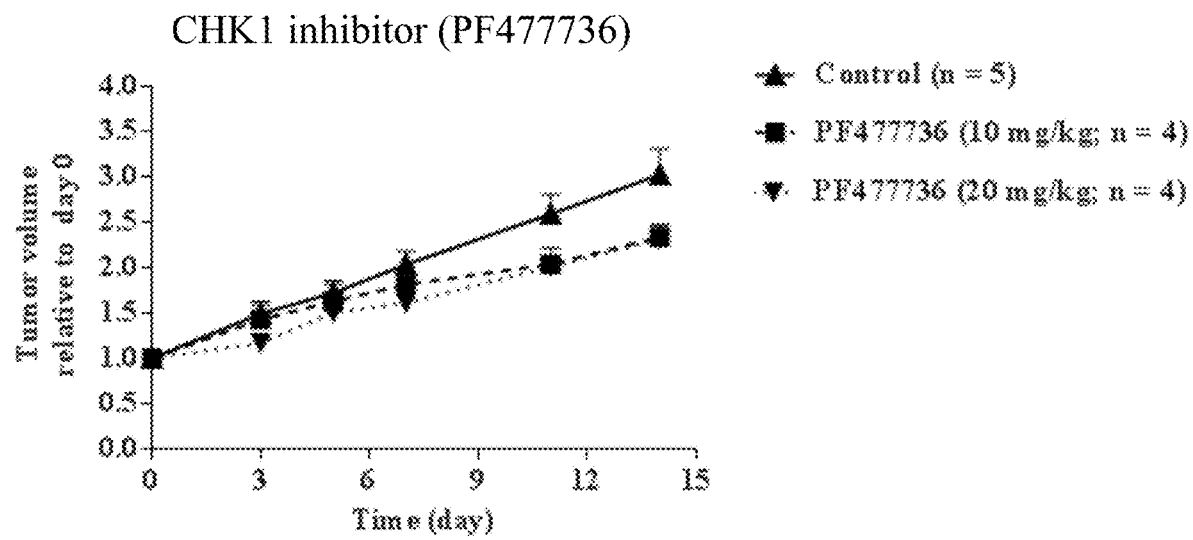
FIGS. 4A-4D are line graphs depicting the effect of the CHK1 inhibitor PF477736 and the PI3K inhibitor BYL719 on OSCC xenografts. SAS cells were injected subcutaneously into NOD/SCID mice, and until the tumors reached 300-500 mm$^3$ in volume, the mice were randomly divided into groups. The engrafted mice were administered vehicle controls, PF477736 at 10 or 20 mg/kg (FIG. 4A), BYL719 at 25 or 50 mg/kg (FIG. 4B), PF477736 (20 mg/kg) plus BYL719 (50 mg/kg) (FIG. 4C), and Cisplatin at 5 mg/kg (FIG. 4D). The tumor volumes were measured and calculated at the indicated times. The data were expressed as the mean S.E.M. The statistical analysis between two groups was performed with Student's t-test. *$p<0.05$; $p<0.01$; *$p<0.001$.
Figure 4B:
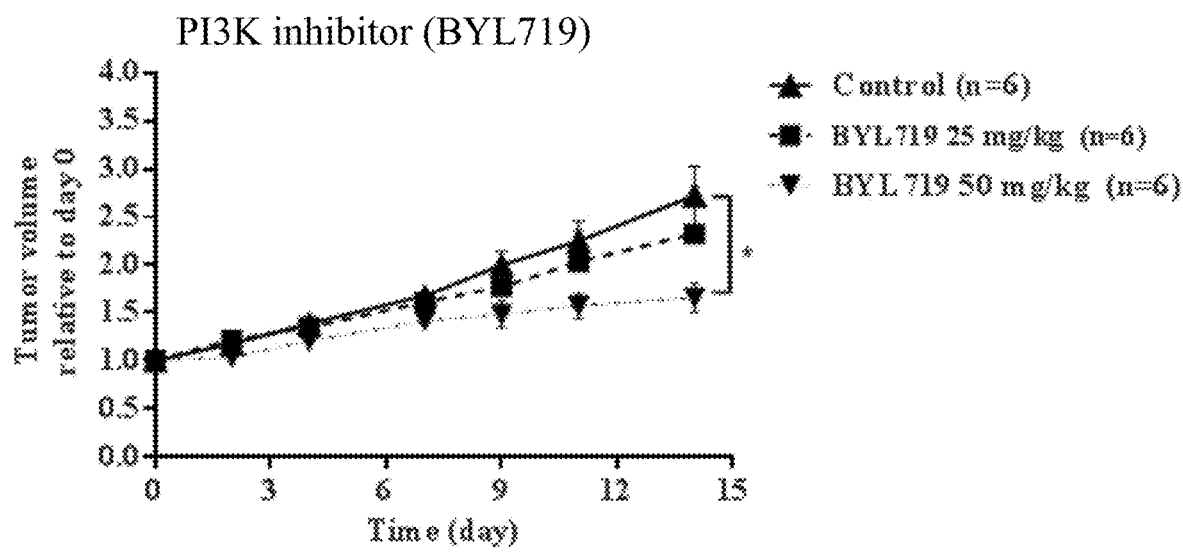
Figure 4C:
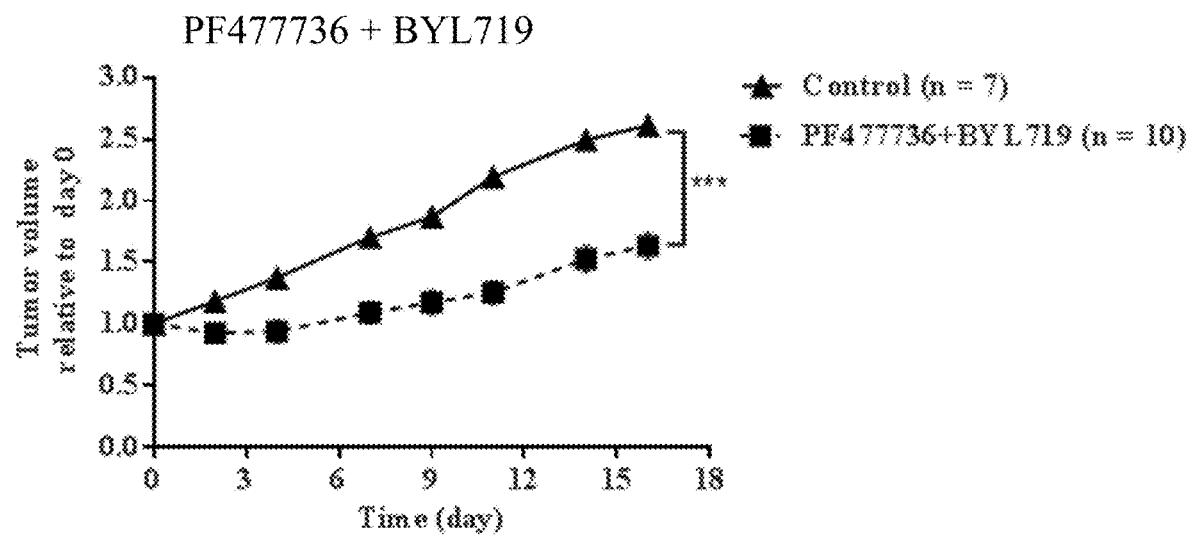
Figure 4D:
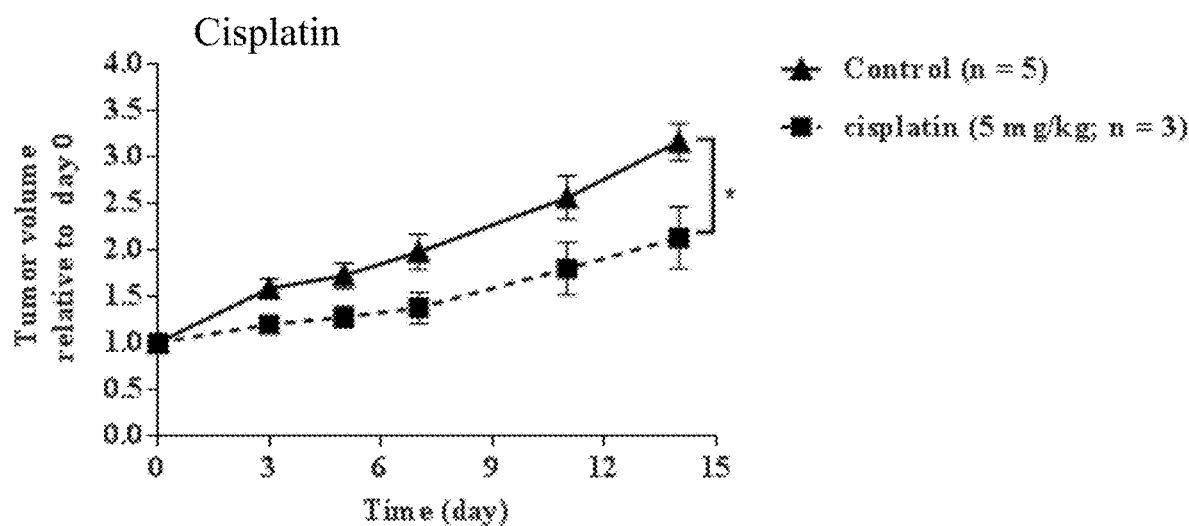

As a proof of concept, SAS cells were used to generate the OSCC in vivo model (hereafter, OSCC CDX). Details for generating OSCC CDX were as described in the "Materials and Methods." Treatments with PF477736 at concentrations of 10 or 20 mg/kg could barely suppress tumor growth as compared with control group (FIG. 4A, 10 mg/kg vs. control, p=0.083; 20 mg/kg vs. control, p=0.081). As to BYL719, treatment in a dose of 50 mg/kg significantly suppressed tumor growth as compared with control group (FIG. 4B, 25 mg/kg vs. control, p=0.508; 50 mg/kg vs. control, p=0.011). Furthermore, co-treatments with PF477736 (20 mg/kg) and BYL719 (50 mg/kg) caused efficient impairment in tumor growth (FIG. 4C, combined treatments vs. control, p<0.01). The data indicated that PF477736 in combination with BYL719 showed an enhanced therapeutic effect; tumor volumes were much smaller in the combined treatment groups. When compared with the current standard chemotherapy Cisplatin in vivo, which exhibited an ability to inhibit tumor growth (FIG. 4D, 5 mg/kg vs. control, p=0.03), the combined treatments with the PF477736 and BYL719 demonstrated superior efficiency in compromising tumor growth in OSCC CDX model.

Example 3 Effects of CHK1 and PI3K Inhibition on OSCC PDX Models

Figure 5A:
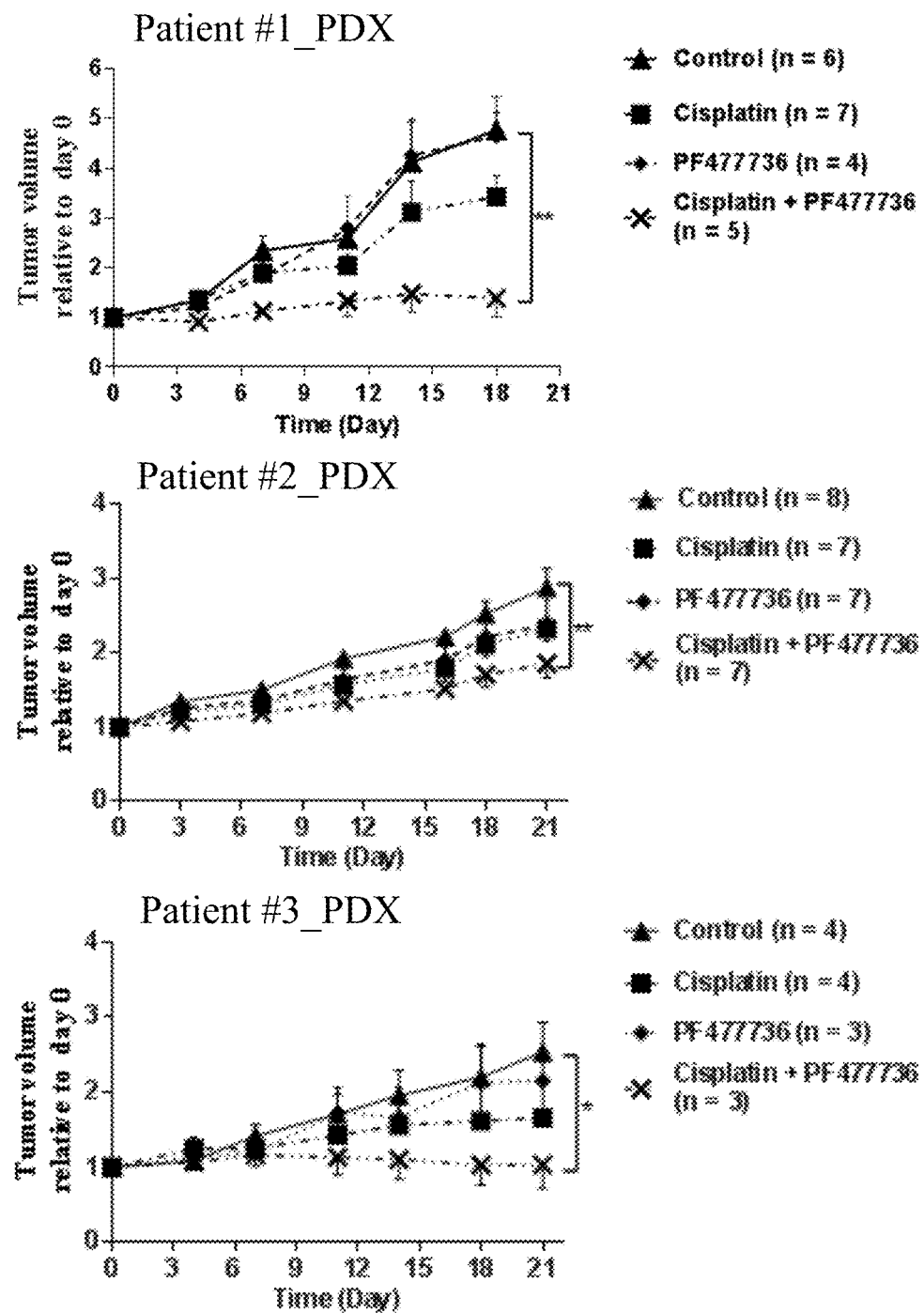
FIGS. 5A-5E illustrate the effects of the CHK1 inhibitor PF477736 in combination with Cisplatin or PI3K inhibitor BYL719 on tumor growth in OSCC patient-derived xenograft (PDX) models.

CHK1 and PI3K inhibitors as a means to manage tumor growth were further evaluated in OSCC PDX models, which are more clinically relevant models. Tumor tissues from three patients with stage IV OSCC (as designated as patient #1, patient #2, patient #3) were used to establish PDX models respectively. The clinical data of the three patients were summarized in Table 3. The genetic profiles of the three patients were characterized by RNA-seq and whole-exome sequencing (data not shown), in which patient #2 had TP53 and CDKN2A mutations, and patient #3 had TP53 mutations and PIK3CA mutations (data not shown). Also, that patient #2 and patient #3 with components in the PI3K/AKT/mTOR signaling pathway significantly enriched was noted (data not shown). The gene expressions of PIK3CA in the three patients were confirmed by qRT-PCR as well, the ratio of PIK3CA expressions were respectively higher than 2.4 in patient #2 and patient #3, but not in patient #1 (data not shown). After the OSCC PDX models were established, the mice were divided into a vehicle control group, Cisplatin group (5 mg/kg), CHK1 inhibitor PF477736 (20 mg/kg) group, and Cisplatin plus PF477736 group (FIG. 5A). The results showed that either Cisplatin or PF477736 single-agent therapy could partially but not significantly inhibit the growth of PDX tumors. In contrast, the combination therapy showed synergistically suppression in tumor growth in all the PDX mouse models (FIG. 5A, combined treatment vs. control, p=0.0024 in patient #1 PDX, p=0.006 in patient #2 PDX, p=0.03 in patient #3 PDX).

Figure 5B:
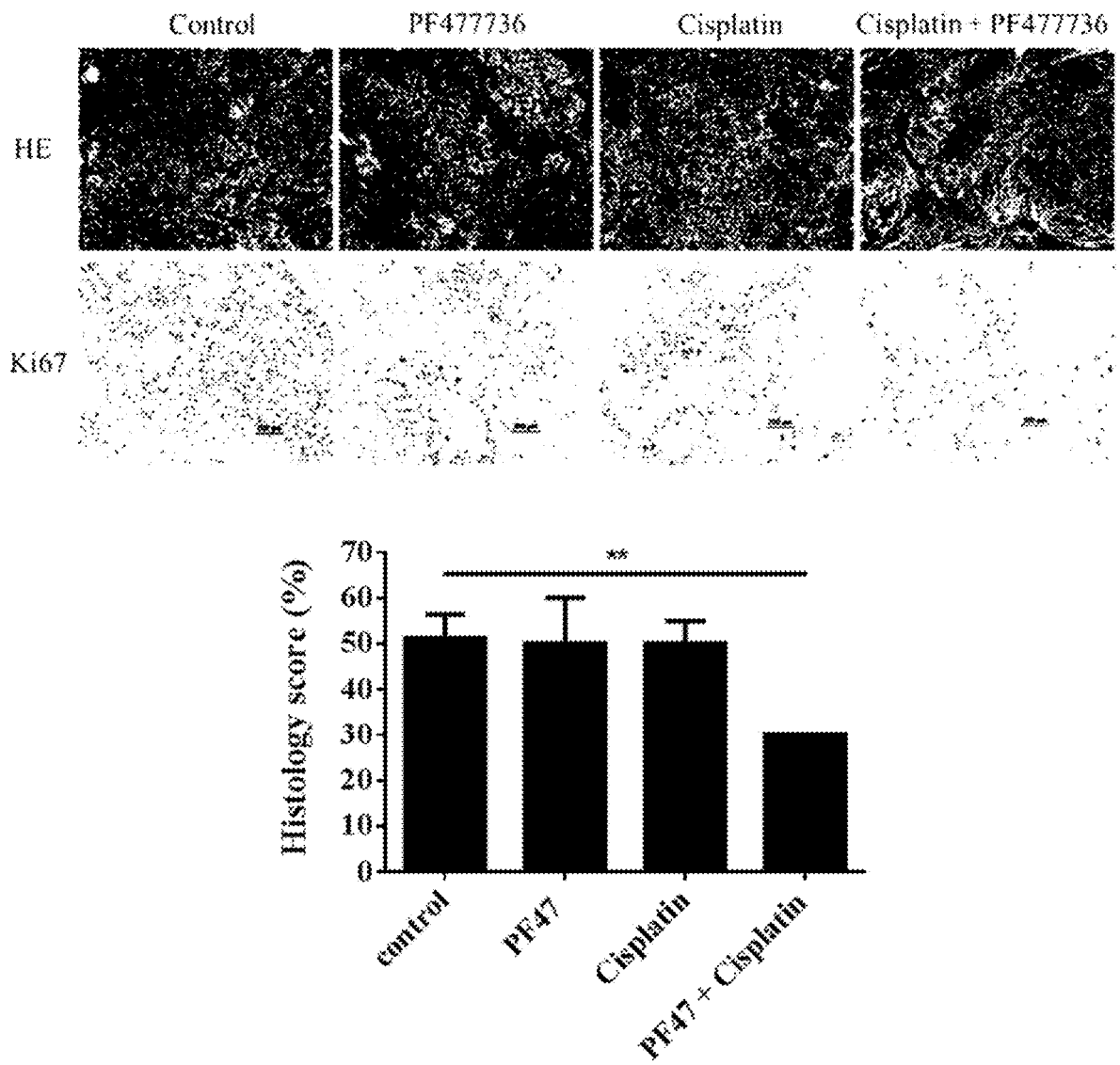

The results of IHC staining of Ki-67, an indicator of cellular proliferation, performed on the xenograft tumor sections were provided in FIG. 5B. Only the combination therapy showed a clear reduction in the amount of Ki-67-positive cells (FIG. 5B).

TABLE 3

Clinical data of the three OSCC patients associated with the present PDX models

| Patient No. | #1 | #2 | #3 |
|---|---|---|---|
| Age (years) | 56 | 47 | 60 |
| Gender | M | M | M |
| T stage | 4A | 4A | 2 |
| N stage | 0 | 2B | 2B |
| Pathology | Well | Moderately | Moderately |
| Overall stage | IV | IV | IV |
| Alcohol drinking | Y | Y | Y |
| Betel quid chewing | Y | Y | Y |
| Cigarette smoking | Y | N | Y |
| Site | Buccal mucosa | Tongue | Buccal mucosa |

Figure 5C:
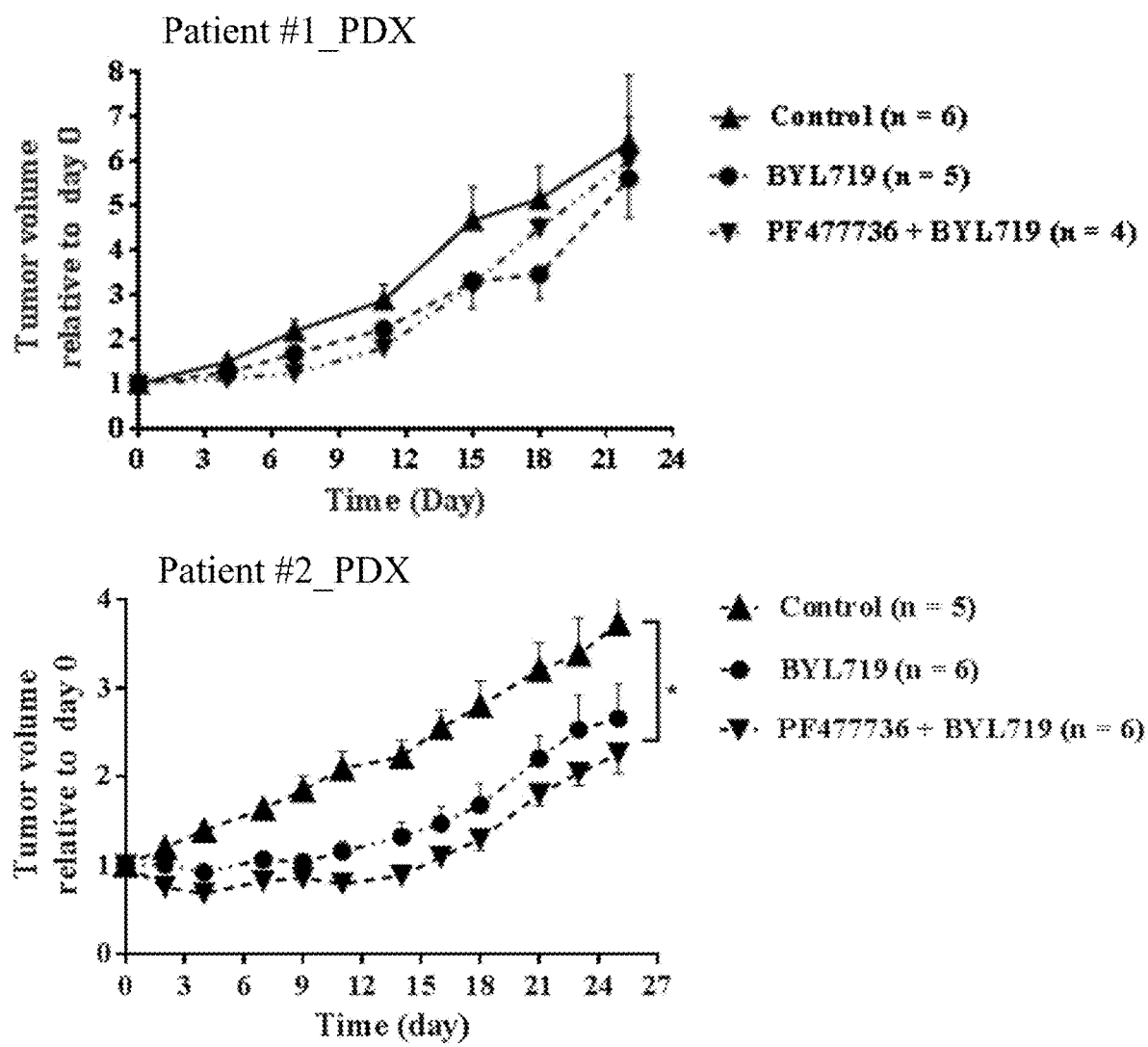
Figure 5D:
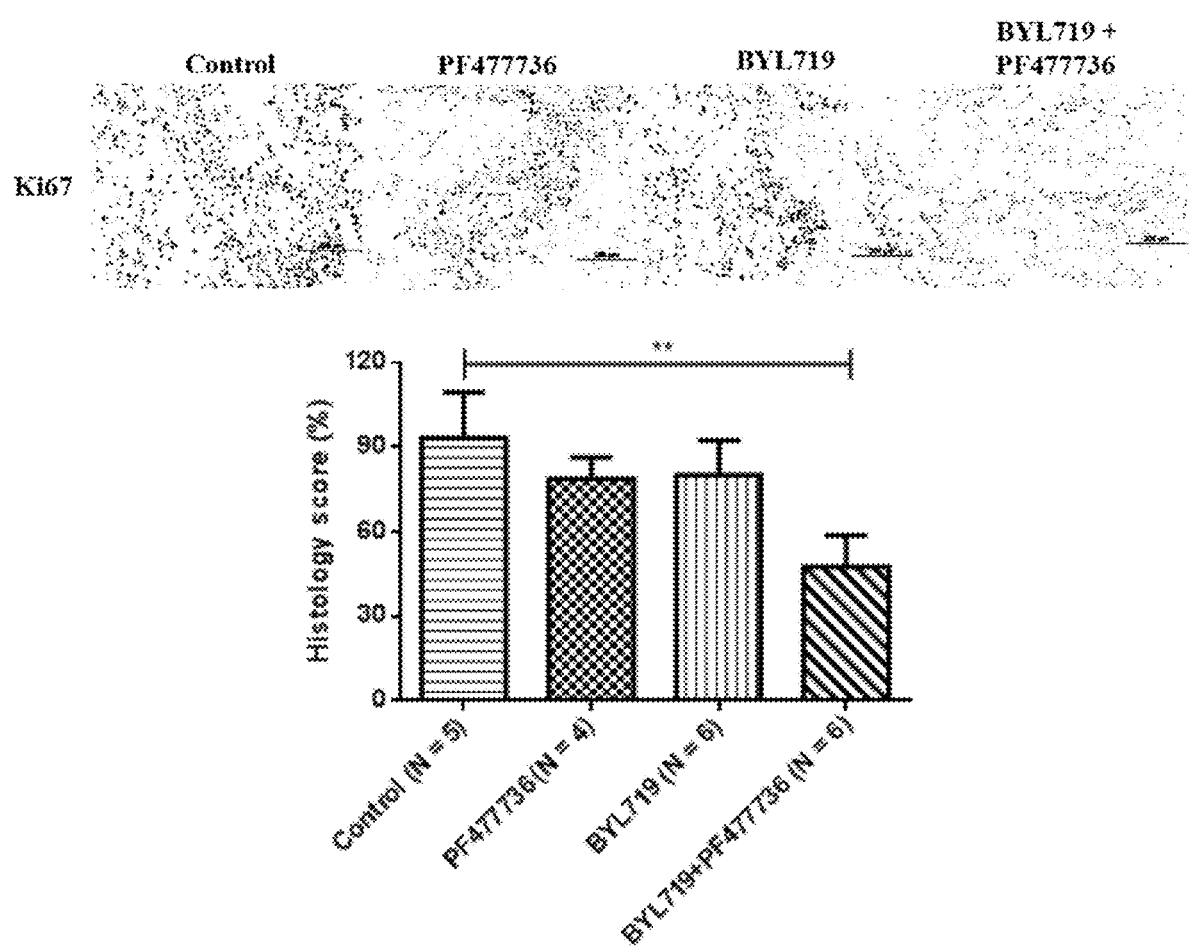
Figure 5E:
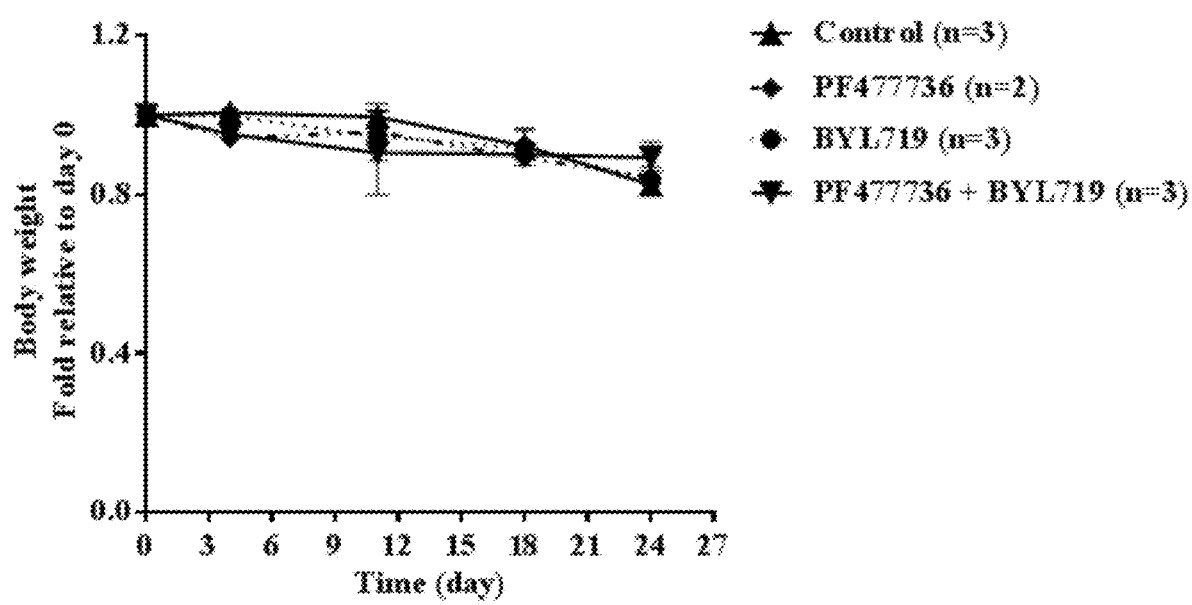

The effects of the combination therapy with CHK1 and PI3K inhibitors on treating different PDX models were investigated as follows (FIG. 5C). BYL719 (50 mg/kg) monotherapy and PF477736 (20 mg/kg) plus BYL719 (50 mg/kg) combined therapy could not inhibit tumor growth in the patient #1's PDX model (FIG. 5C, upper panel; p=0.66 in BYL719 monotherapy vs. control; p=0.844 in combined treatment vs. control). In the meanwhile, BYL719 (50 mg/kg) monotherapy slightly inhibited tumor growth (50 mg/kg vs. control, p=0.16), whereas BYL719 (50 mg/kg) plus PF477736 (20 mg/kg) combined therapy synergistically slowed down tumor growth in the patient #2 PDX (FIG. 5C, lower panel, combined treatment vs. control, p=0.036). Patient #2's PDX with the specified genetic signatures (higher CHEK1 and PIK3CA expression) showed more responsiveness to the BYL719 plus PF477736 combination therapy. Moreover, as shown in FIG. 5D, the Ki-67-positive cells were significantly decreased in the BYL719 plus PF477736 combined treatments, indicating a reduction in cancer cell proliferation under such treatments. In addition, no significant weight loss was observed in any treatment groups in the patient #2 PDX model (FIG. 5E).

In conclusion, the data provided in the present disclosure suggest that CHK1 inhibitors alone or in combination with chemotherapy (e.g., Cisplatin) may be more effective in treating cancer patients with higher expression of CHEK1 alone.

Furthermore, PI3K inhibitors plus CHK1 inhibitors may serve as a promising anti-cancer treatment in treating cancer patients with higher expression of both CHEK1 and PIK3CA PIK3CD. Patients with the specific genetic signatures as described herein may particularly benefit from personalized anti-cancer treatments as described in the present disclosure.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A method for treating an oral cancer in a subject, comprising,
   (a) respectively obtaining a first and a second biological samples from a lesion site and a non-lesion site of the subject;
   (b) respectively measuring the expression levels of a biomarker in the first and the second biological samples by quantitative reverse transcription polymerase chain reaction (qRT-PCR) thereby obtaining a first expression level and a second expression level, wherein the biomarker is CHEK1 gene, PIK3CA gene, or PIK3CD gene;
   (c) determining the ratio of the first expression level to the second expression level; and
   (d) administering to the subject an effective amount of a checkpoint kinase 1 inhibitor or a phosphatidylinositol 3-kinase inhibitor when the biomarker is the CHEK1 gene, and the ratio determined in the step (c) is at least 1.7; or when the biomarker is the PIK3CA gene, and the ratio determined in the step (c) is at least 2.4;
   or when the biomarker is the PIK3CD gene, and the ratio determined in the step (c) is at least 3.1;
wherein in the qRT-PCR,
   a primer pair of SEQ ID NOs: 1 and 2 is used for detecting the expression level of the CHEK1 gene:
   a primer pair of SEQ ID NOs: 3 and 4 is used for detecting the expression level of the PIK3CA gene; and
   a primer pair of SEQ ID NOs: 5 and 6 is used for detecting the expression level of the PIK3CD gene.

2. The method of claim 1, wherein the oral cancer is oral squamous cell carcinoma (OSCC).

3. The method of claim 1, wherein the checkpoint kinase 1 inhibitor is selected from the group consisting of,
   (S)-5-(3-Fluorophenyl)-N-(piperidin-3-yl)-3-ureidothiophene-2-carboxamide;
   4-(((3S)-1-Azabicyclo(2.2.2)oct-3-yl)amino)-3-(1H-benzimidazol-2-yl)-6-chloroquin olin-2(1H)-one (CHIR-124);
   Rabusertib;
   Prexasertib;
   4-(2,6-dichlorophenyl)-9-hydroxy-6-(3-(methylamino)propyl)pyrrolo[3,4-c]carbazole-1,3(2H,6H)-dione (PD-321852);
   (R)-2-amino-2-cyclohexyl-N-(2-(1-methyl-1H-pyrazol-4-yl)-6-oxo-5,6-dihydro-1H-[1, 2]diazepino[4,5,6-cd]indol-8-yl)acetamide;
   (R)-6-Bromo-3-(1-methyl-1H-pyrazol-4-yl)-5-(piperidin-3-yl)pyrazolo[1,5-a]pyrimidi n-7-amine;
   (R)-N-(4-(3-aminopiperidin-1-yl)-5-bromo-1H-pyrrolo[2,3-b]pyridin-3-yl)nicotinami de;
   (R)-N-(4-(3-aminopiperidin-1-yl)-5-bromo-1H-pyrrolo[2,3-b]pyridin-3-yl isobutyramide;
   (R)-N-(5-bromo-4-(3-(methylamino)piperidin-1-yl)-1H-pyrrolo[2,3-b]pyridin-3-yl)nic otinamide;
   (R)-N-(4-(3-aminopiperidin-1-yl)-5-bromo-1H-pyrrolo[2,3-b]pyridin-3-yl)-5-methyln icotinamide;
   (R)-N-(4-(3-aminopiperidin-1-yl)-5-bromo-1H-pyrrolo[2,3-b]pyridin-3-yl)cyclopropa necarboxamide;
   (R)-N-(4-(3-aminopiperidin-1-yl)-5-bromo-1H-pyrrolo[2,3-b]pyridin-3-yl)-3-methylb utanamide; and
   (R)-N-(4-(3-aminopiperidin-1-yl)-5-bromo-1H-pyrrolo[2,3-b]pyridin-3-yl)-2-cyclopro pylacetamide.

4. The method of claim 3, wherein the checkpoint kinase 1 inhibitor is (S)-5-(3-Fluorophenyl)-N-(piperidin-3-yl)-3-ureidothiophene-2-carboxamide; Prexasertib; or
   (R)-2-amino-2-cyclohexyl-N-(2-(1-methyl-1H-pyrazol-4-yl)-6-oxo-5,6-dihydro-1H-[1, 2]diazepino[4,5,6-cd]indol-8-yl)acetamide.

5. The method of claim 1, wherein the phosphatidylinositol 3-kinase inhibitor is selected from the group consisting of,
   (2S)-N1-[5-(2-tert-butyl-4-thiazolyl)-4-methyl-2-thiazolyl]pyrrolidine-1,2-dicarboxa mide;
   (Z)-5-((5-(4-fluoro-2-hydroxyphenyl)furan-2-yl)methylene)thiazolidine-2,4-dione;
   5-(2,2-Difluoro-benzo[1,3]dioxol-5-ylmethylene)-thiazolidine-2,4-dione;
   (R)-2-(1-(7-methyl-2-morpholino-4-oxo-4H-pyrido[1,2-a]pyrimidin-9-yl)ethylamino) benzoic acid;
   2-amino-N-[7-methoxy-8-(3-morpholinopropoxy)-2,3-dihydroimidazo[1,2-c]quinazol in;
   Copanlisib;
   8-(6-methoxypyridin-3-yl)-3-methyl-1-(4-(piperazin-1-yl)-3-(trifluoromethyl)phenyl)-1H-imidazo[4,5-c]quinolin-2(3H)-one maleate;
   Buparlisib;
   Alpelisib;
   (5E)-5-{[5-(4-fluorophenyl)furan-2-yl]methylidene}-1,3-thiazolidine-2,4-dione;
   5-(2-Amino-8-fluoro-[1,2,4]triazolo[1,5-a]pyridin-6-yl)-N-tert-butylpyridine-3-sulfon amide;
   Duvelisib;
   2-((6-amino-9H-purin-9-yl)methyl)-5-methyl-3-o-tolylquinazolin-4(3H)-one;
   Idelalisib;
   Serabelisib;
   Taselisib;
   Pictilisib;
   Apitolisib;
   (Z)-5-((4-(pyridin-4-yl)quinolin-6-yl)methylene)thiazolidine-2,4-dione;

Omipalisib;
2-methyl-1-(2-methyl-3-(trifluoromethyl)benzyl)-6-morpholino-1H-benzo[d]imidazol e-4-carboxylic acid;
6-[5-[(phenylsulfonyl)amino]-3-pyridinyl]-imidazo[1,2-a]pyridine-3-carboxylic acid, ethyl ester;
2-amino-N,N-dimethyl-5-(3-(2-methylpyridin-4-yl)-1H-pyrrolo[2,3-b]pyridine-5-yl)p yridine-3-sulfonamide;
2-(4-Morpholinyl)-8-phenyl-4H-1-benzopyran-4-one;
Dactolisib;
Perifosine;
2-Amino-8-[4-(2-hydroxyethoxy)cyclohexyl]-6-(6-methoxypyridin-3-yl)-4-methylpyr ido[2,3-d]pyrimidin-7-one;
Gedatolisib;
3-(4-morpholinopyrido[3',2':4,5]furo[3,2-d]pyrimidin-2-yl)Phenol;
2-methyl-5-nitro-2-[(6-bromoimidazo[1,2-a]pyridin-3-yl)methylene]-1-methylhydrazi de-benzenesulfonic acid;
N-(2,3-dihydro-7,8-dimethoxyimidazo[1,2-c]quinazolin-5-yl)-3-pyridinecarboxamide;
2-[(4-amino-1H-pyrazolo[3,4-d]pyrimidin-1-yl)methyl]-5-methyl-3-(2-methylphenyl)-4(3H)-quinazolinone;
2-[[4-amino-3-(3-hydroxyphenyl)-1H-pyrazolo[3,4-d]pyrimidin-1-yl]methyl]-5-meth yl-3-(2-methylphenyl)-4(3H)-quinazolinone;
1-(4-(3-ethyl-7-morpholino-3H-[1,2,3]triazolo[4,5-d]pyrimidin-5-yl)phenyl)-3-(4-(4-methylpiperazine-1-carbonyl)phenyl)urea;
Sonolisib;
(S)-2-(2-(2-Methylindolin-1-yl)-2-oxoethyl)-6-morpholinopyrimidin-4(3H)-one;
Pilaralisib;
(2S)-2-[[(2S)-3-Carboxy-2-[[2-[[(2S)-5-(diaminomethyl-ideneamino)-2-[[4-oxo-4-[[4-(4-oxo-8-phenyl-chromen-2-yl)morpholin-4-ium-4-yl]methoxy]butanoyl]amino]penta noyl]amino]acetyl]amino] propanoyl]amino]-3-hydroxypropanoate;
3-(2,4-Diaminopteridin-6-yl)phenol;
Umbralisib;
5-(9-Isopropyl-8-methyl-2-morpholino-9H-purin-6-yl) pyrimidin-2-amine;
Voxtalisib; and
4,4'-(6-(2-(Difluoromethyl)-1H-benzo[d]imidazol-1-yl)-1,3,5-triazine-2-diyl)dimor pholine.

6. The method of claim 5, wherein the phosphatidylinositol 3-kinase inhibitor is Alpelisib;
Pictilisib; or
(Z)-5-((4-(pyridin-4-yl)quinolin-6-yl)methylene)thiazolidine-2,4-dione.

7. The method of claim 1, further comprising administering to the subject an anti-cancer treatment selected from the group consisting of, surgery, radiotherapy, chemotherapy, immunotherapy, and a combination thereof, prior to, in conjunction with, or subsequent to the step (d).

8. The method of claim 7, wherein the chemotherapy is conducted by administering to the subject a chemotherapeutic agent selected from the group consisting of, Bleomycin, Carboplatin, Capecitabine, Cisplatin, Docetaxel, 5-Fluorouracil (5-FU), Hydroxyurea, Methotrexate, and Paclitaxel.

9. The method of claim 8, wherein the chemotherapeutic agent is Cisplatin.

10. The method of claim 1, wherein the subject is a human.

* * * * *

SEQUENCE LISTING

<160> NUMBER OF SEQ ID NOS: 8

<210> SEQ ID NO 1
<211> LENGTH: 21

<212> TYPE: DNA
<213> ORGANISM: Artificial Sequence
<220> FEATURE:
<223> OTHER INFORMATION: Synthetic

<400> SEQUENCE: 1
tcggtataat aatcgtgagc g          21

<210> SEQ ID NO 2
<211> LENGTH: 20
<212> TYPE: DNA
<213> ORGANISM: Artificial Sequence
<220> FEATURE:
<223> OTHER INFORMATION: Synthetic

<400> SEQUENCE: 2
acaggaccaa acatcaactg            20

<210> SEQ ID NO 3
<211> LENGTH: 19
<212> TYPE: DNA
<213> ORGANISM: Artificial Sequence
<220> FEATURE:
<223> OTHER INFORMATION: Synthetic

<400> SEQUENCE: 3
acgatggaca actgtttca             19

<210> SEQ ID NO 4
<211> LENGTH: 19
<212> TYPE: DNA
<213> ORGANISM: Artificial Sequence
<220> FEATURE:
<223> OTHER INFORMATION: Synthetic

<400> SEQUENCE: 4
gtctttgtgc attcttggg             19

<210> SEQ ID NO 5
<211> LENGTH: 21
<212> TYPE: DNA
<213> ORGANISM: Artificial Sequence
<220> FEATURE:
<223> OTHER INFORMATION: Synthetic

<400> SEQUENCE: 5
gacatccagt atctcaagga c          21

<210> SEQ ID NO 6
<211> LENGTH: 18
<212> TYPE: DNA
<213> ORGANISM: Artificial Sequence
<220> FEATURE:
<223> OTHER INFORMATION: Synthetic

<400> SEQUENCE: 6
agccagttca ctttggtt              18

<210> SEQ ID NO 7
<211> LENGTH: 23
<212> TYPE: DNA
<213> ORGANISM: Artificial Sequence
<220> FEATURE:
<223> OTHER INFORMATION: Synthetic

<400> SEQUENCE: 7

```
tgctcacccc accaacaatt tag                                           23

<210> SEQ ID NO 8
<211> LENGTH: 26
<212> TYPE: DNA
<213> ORGANISM: Artificial Sequence
<220> FEATURE:
<223> OTHER INFORMATION: Synthetic

<400> SEQUENCE: 8
ctgggtttga tcattctgta gattaa                                        26
```